US009982733B2

(12) United States Patent
Shih

(10) Patent No.: US 9,982,733 B2
(45) Date of Patent: May 29, 2018

(54) FORCE-LIMITING AND DAMPING DEVICE

(71) Applicant: Jui-Yuan Shih, Changhua Hsien (TW)

(72) Inventor: Jui-Yuan Shih, Changhua Hsien (TW)

( * ) Notice: Subject to any disclaimer, the term of this patent is extended or adjusted under 35 U.S.C. 154(b) by 0 days. days.

(21) Appl. No.: 15/335,572

(22) Filed: Oct. 27, 2016

(65) Prior Publication Data
US 2017/0211646 A1 Jul. 27, 2017

(30) Foreign Application Priority Data

Jan. 26, 2016 (TW) .............................. 105102409 A

(51) Int. Cl.
| | | |
|---|---|---|
| *B25D 1/12* | (2006.01) | |
| *F16F 1/04* | (2006.01) | |
| *A61B 17/92* | (2006.01) | |
| *B26B 23/00* | (2006.01) | |
| *A63B 60/54* | (2015.01) | |
| *B25D 1/06* | (2006.01) | |
| *B25G 1/10* | (2006.01) | |
| *F16F 1/12* | (2006.01) | |

(Continued)

(52) U.S. Cl.
CPC ................ *F16F 1/04* (2013.01); *A61B 17/92* (2013.01); *A63B 53/04* (2013.01); *A63B 60/54* (2015.10); *B25D 1/06* (2013.01); *B25D 1/12* (2013.01); *B25G 1/102* (2013.01); *B26B 23/00* (2013.01); *F16F 1/12* (2013.01); *A61C 8/0089* (2013.01); *A63B 53/0466* (2013.01); *A63B 2053/0416* (2013.01)

(58) Field of Classification Search
CPC .... F16F 1/04; F16F 1/12; A63B 60/54; A63B 53/04; A63B 53/0466; A63B 2053/0416; A61B 17/92; B25D 1/06; B25D 1/12; B25G 1/102; B26B 23/00; A61C 8/0089
See application file for complete search history.

(56) References Cited

U.S. PATENT DOCUMENTS

| | | |
|---|---|---|
| 1,045,145 A | 11/1912 | Hubbard |
| 1,118,010 A | 11/1914 | Huhn |

(Continued)

FOREIGN PATENT DOCUMENTS

| | | |
|---|---|---|
| CH | 408541 A | 2/1966 |
| CN | 2210757 Y | 10/1995 |

(Continued)

*Primary Examiner* — Robert Scruggs
(74) *Attorney, Agent, or Firm* — Alan D. Kamrath; Kamrath IP Lawfirm, P.A.

(57) ABSTRACT

A force-limiting and damping device has a body, a tapping element, and an elastic element. The body has a connecting segment and a holding segment. The connecting segment is formed on an end of the body and has a mounting hole. The holding segment is formed on the body opposite the connecting segment. The tapping element is connected to the body to move relative to the connecting segment. The elastic element is mounted between the tapping element and the connecting segment to abut against the tapping element and to enable the tapping element to move relative to the connecting segment. The structural relationship between the connecting segment, the tapping element, and the elastic element may provide a delayed rebound and damping effect to the reaction force, and the applied force is continuously transferred to a tapping object. This may reduce noise and the loss of energy.

62 Claims, 36 Drawing Sheets

(51) Int. Cl.
  *A63B 53/04*  (2015.01)
  *A61C 8/00*  (2006.01)

(56) References Cited

U.S. PATENT DOCUMENTS

| | | | |
|---|---|---|---|
| 1,463,861 | A | 8/1923 | Winkley |
| 2,923,191 | A * | 2/1960 | Fulop .................... B25B 21/023 |
| | | | 173/203 |
| 2,928,444 | A | 3/1960 | Ivins |
| 3,030,989 | A | 4/1962 | Elliott |
| 5,282,805 | A | 2/1994 | Richelsoph et al. |
| 5,586,948 | A | 12/1996 | Mick |
| 6,016,722 | A | 1/2000 | Gierer et al. |
| 6,128,977 | A | 10/2000 | Gierer et al. |
| 6,370,993 | B1 * | 4/2002 | Pitstick .................... B25B 19/00 |
| | | | 173/203 |
| 2002/0148330 | A1 * | 10/2002 | Huang .................... B25C 3/002 |
| | | | 81/23 |
| 2003/0167880 | A1 * | 9/2003 | Yamakawa .............. G04D 1/10 |
| | | | 81/6 |
| 2008/0293010 | A1 * | 11/2008 | Song .................... A61C 8/0089 |
| | | | 433/165 |
| 2015/0196343 | A1 * | 7/2015 | Donald .................. A61B 17/92 |
| | | | 606/100 |

FOREIGN PATENT DOCUMENTS

| | | |
|---|---|---|
| CN | 101987444 A | 3/2011 |
| CN | 203003824 U | 6/2013 |
| CN | 203156702 U | 8/2013 |
| TW | 424656 U | 3/2001 |

* cited by examiner

FORCE-LIMITING AND DAMPING DEVICE

BACKGROUND OF THE INVENTION

1. Field of the Invention

The present invention relates to a force-limiting and damping device and, more particularly, to a force-limiting and damping device that may provide a damping effect to a user, may provide a high stability in use and may be easily adjusted.

2. Description of Related Art

A conventional hammer or mallet in the industry is used to tap nails in wood, cement walls or metal plates. During the tapping process, the conventional hammer or mallet may bounce by a reaction force, and this will shorten the contacting time of a tapping face of the conventional hammer or mallet relative to the nails, and will tend to make the nails bend or deflect. Furthermore, the instant rebound reaction force will be converted into heat and noise as energy dissipation, and this will reduce the tapping efficiency of the user. That is, the applied force that is provided by the user is not tapped on the nails sufficiently. The user needs to tap the nails repeatedly to enable the nails to knock and fix in wooden or metal plates, and this will increase the numbers and time of tapping the nails. In addition, when the user holds a handle of the conventional hammer or mallet, the vibration generated during the bouncing process also make the user feel uncomfortable.

Additionally, a conventional medical or surgical hammer has a similar structure as the industrial hammer, and the tapping face of the conventional surgical or surgery hammer is mostly a rigid structure. Therefore, when dentists use the conventional medical or surgical hammer a dental surgery, the returning vibration generated by the reaction force will make the dentists feel uncomfortable and will make it difficult to firmly hold the conventional medical or surgery hammer. The patient will feel pain due to the tapping force and may even have a concussion.

Furthermore, a conventional golf club has a tapping head being a rigid structure. Therefore, when the tapping head of the conventional golf club hits a ball, the conventional golf club has an instant rebound reaction force and makes the user feel uncomfortable. Additionally, the contacting time between the tapping head and the ball is short, and the user cannot effectively control the ball. This will affect the user's performance.

According to the above-mentioned description, since each one of the conventional industrial hammer or mallet, the conventional medical or surgical hammer, and the conventional golf club has a rigidity tapping face or tapping head, an instant rebound reaction force may be generated by the rigid tapping face or tapping head in use, and noise and discomfort are also generated during the tapping process. This will affect the smoothness and control of operation.

SUMMARY OF THE INVENTION

The main objective of the invention is to provide a force-limiting and damping device that may provide a damping effect to a user, may provide a high stability in use and may be easily adjusted.

A force-limiting and damping device in accordance with the present invention has a body, a tapping element, and an elastic element. The body has a connecting segment and a holding segment. The connecting segment is formed on an end of the body and has a mounting hole. The holding segment is formed on the body opposite the connecting segment. The tapping element is connected to the body to move relative to the connecting segment. The elastic element is mounted between the tapping element and the connecting segment to abut against the tapping element and to enable the tapping element to move relative to the connecting segment. The structural relationship between the connecting segment, the tapping element, and the elastic element may provide a delayed rebound and damping effect to the reaction force, and the applied force is continuously transferred to a tapping object. This may reduce the loss of energy and noise.

Other objectives, advantages and novel features of the invention will become more apparent from the following detailed description when taken in conjunction with the accompanying drawings.

DETAILED DESCRIPTION OF PREFERRED EMBODIMENTS

Figure 1:
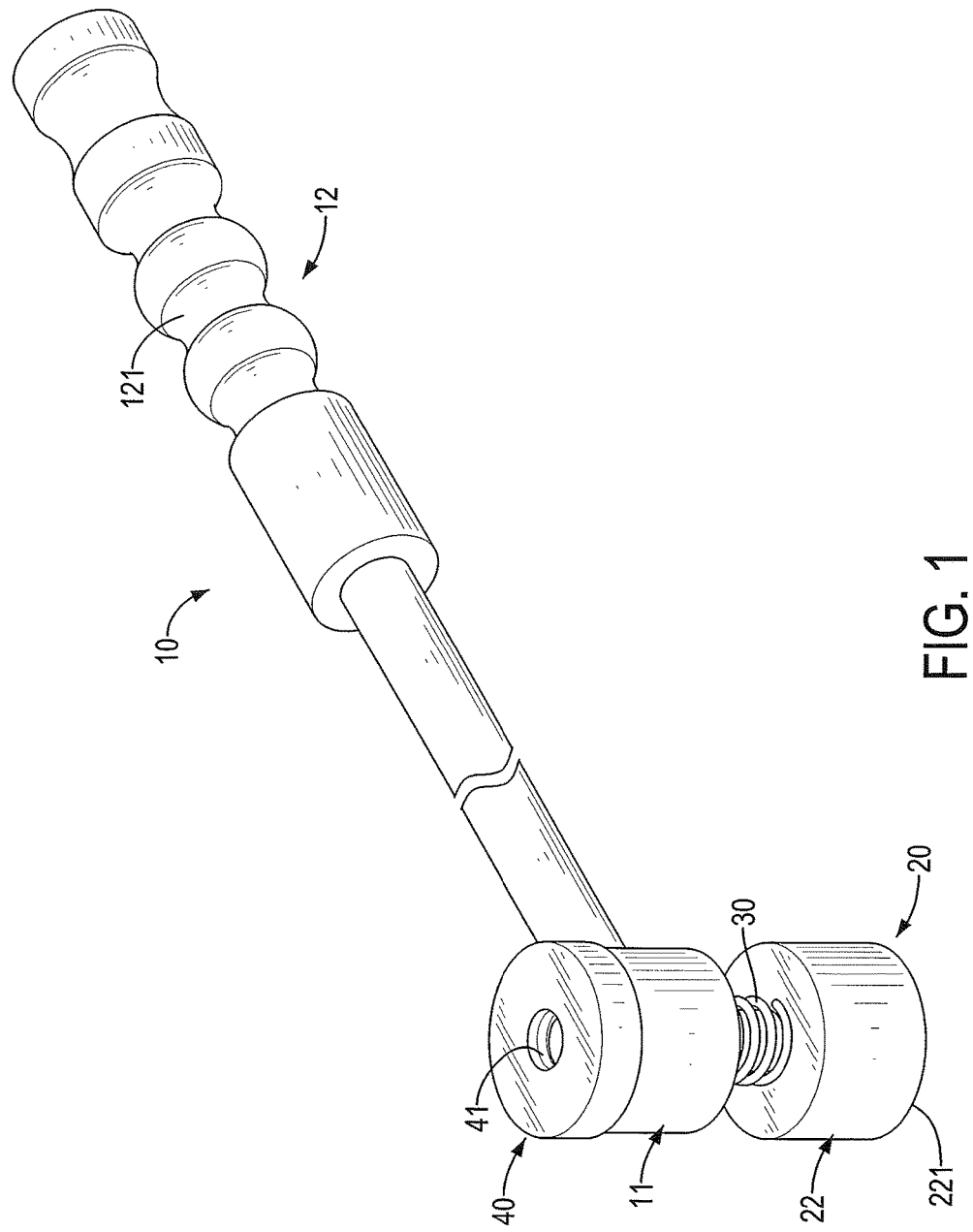
FIG. 1 is a perspective view of a first embodiment of a force-limiting and damping device in accordance with the present invention.
Figure 2:
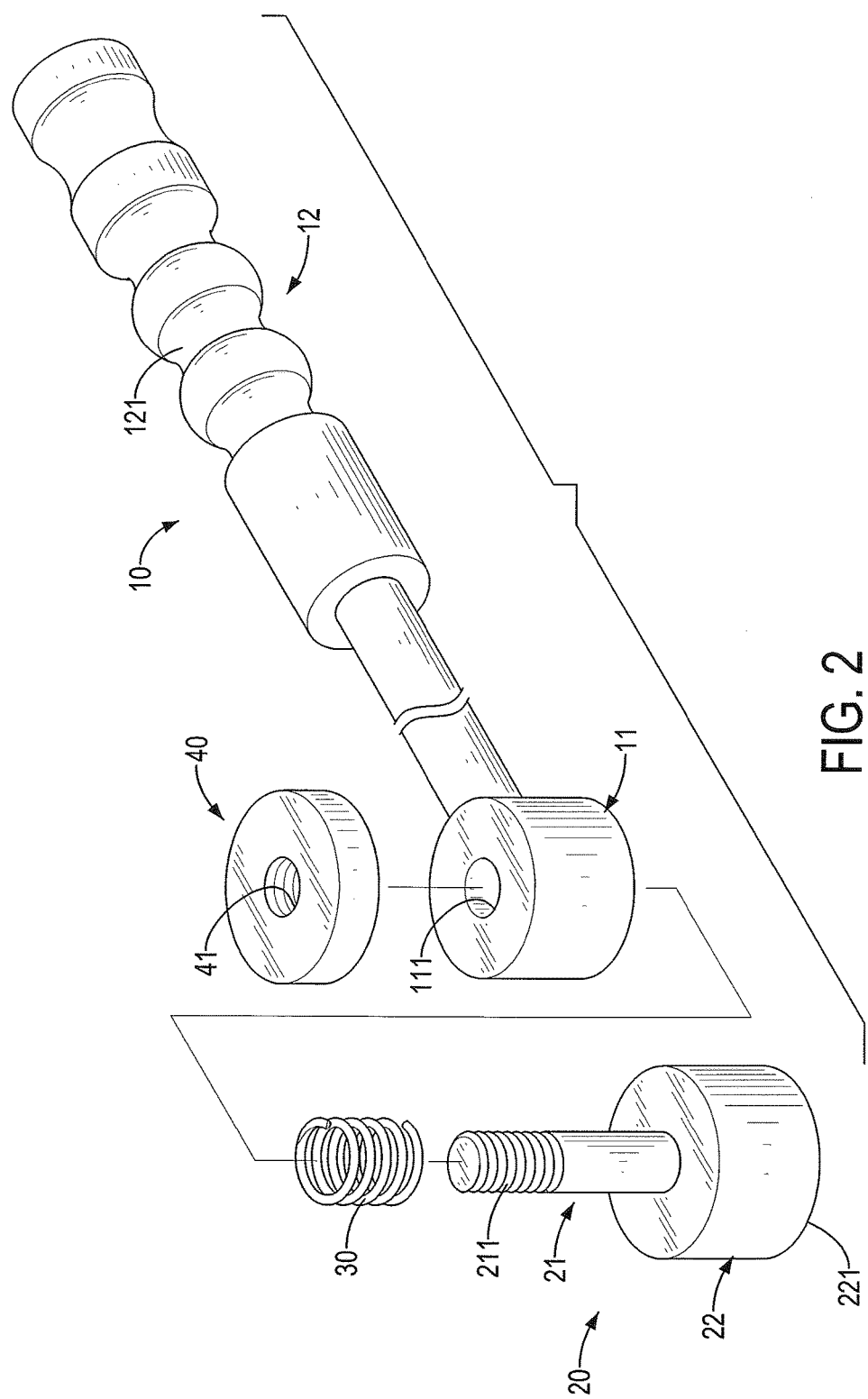
FIG. 2 is an exploded perspective view of the force-limiting and damping device in FIG. 1.
Figure 3:
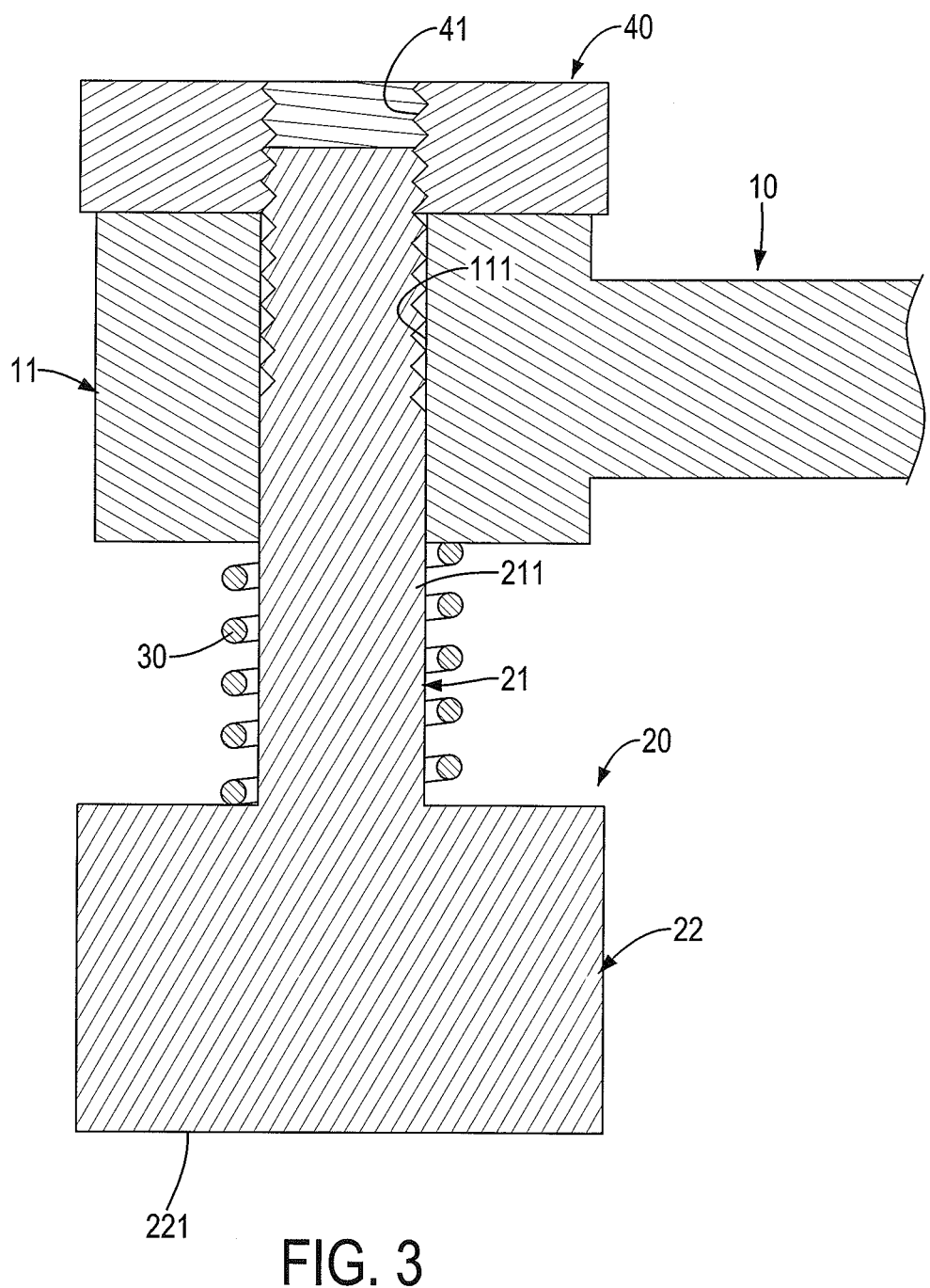
FIG. 3 is an enlarged cross sectional side view of the force-limiting and damping device in FIG. 1.

With reference to FIGS. 1 to 3, a first embodiment of a force-limiting and damping device in accordance with the present invention comprises a body 10, a tapping element 20, an elastic element 30, and a locking element 40.

The body 10 may be an elongated shaft, and has a front end, a rear end, a connecting segment 11, and a holding segment 12.

The connecting segment 11 may be tubular, is formed on and protrudes from the front end of the body 10, and has a top side, a bottom side, an external surface, and a mounting hole 111. The mounting hole 111 is axially formed through the top side and the bottom side of the connecting segment 11. The holding segment 12 is formed on the rear end of the body 10, is opposite the connecting segment 11, and has an external surface and a skidproof structure. The skidproof structure is deposited on the external surface of the holding segment 12. Additionally, the skidproof structure has multiple annular grooves 121 formed in the external surface of the holding segment 12 at spaced intervals to enable a user to hold the holding segment 12 of the body 10 firmly.

The tapping element 20 is connected to the body 10 to move relative to the connecting segment 11, and has a mounting segment 21 and a tapping segment 22.

The mounting segment 21 is movably connected to the connecting segment 11 of the body 10. Furthermore, the mounting segment 21 is a rod that extends through the mounting hole 111 of the connecting segment 11. Additionally, the mounting segment 21 has a cross section corresponding to a cross section of the mounting hole 111. When the cross section of the mounting segment 21 is round, the mounting segment 21 may be rotated relative to the connecting segment 11. Furthermore, when the cross section of the mounting segment 21 is polygonal, the mounting segment 21 only can move relative to the connecting segment 11 without rotating.

The mounting segment 21 has an external surface, a holding end, a forming end, and a locking structure 211. The holding end of the mounting segment 21 extends out of the top side of the connecting segment 11 via the mounting hole 111. The forming end of the mounting segment 21 extends out of the bottom side of the connecting segment 11 via the mounting hole 111. The locking structure 211 may be an outer screw, and is deposited on the external surface of the mounting segment 21 adjacent to the holding end of the mounting segment 21.

The tapping segment 22 is deposited on the forming end of the mounting segment 21, is opposite the locking structure 211, and is mounted below the connecting segment 11. Additionally, the tapping segment 22 is integrally formed with the mounting segment 21, and may be made of metal, polyethylene (PE), hard material such as plastic, or elastic materials such as rubber, silicone or wood. Furthermore, the tapping segment 22 may be made of magnetic metal to enable the tapping segment 22 to attract a nail in use. The tapping segment 22 may be a spheroid. Additionally, the tapping segment 22 has a tapping face 221 deposited on a bottom of the tapping segment 22, and the tapping face 221 may be made of metal, polyethylene (PE), hard material such as plastic, or elastic materials such as rubber, silicone, wood or leather. In addition, the tapping face 221 may be planar, spherical, or any other shape.

The elastic element 30 is mounted on the mounting segment 21 of the tapping element 20, and abuts against the connecting segment 11 of the body 10 and the tapping segment 22 of the tapping element 20. The elastic element 30 may be made of flexible material in a fixed shape such as a spring, rubber, silicone, a metal washer, a flexible metal block or a flexible block. Furthermore, the spring may be mounted in the rubber or the silicone to form the elastic element 30.

Additionally, when the elastic element 30 is a spring, the spring may have a uniform inner diameter (the inner diameter is the same at a top end and a bottom end of the spring) or have different inner diameters (the inner diameter at the top end of the spring is wider than the inner diameter at the bottom end of the spring). When using a spring with a uniform inner diameter as the elastic element 30, each portion of the spring may be knocked against each other during a tapping process of the force-limiting and damping device. When using a spring with different inner diameters, each portion of the spring may not be knocked against each other during a tapping process of the force-limiting and damping device. Further, in use, different elastic forces of the elastic elements 30 can be selected, and the elastic element 30 can be pre-compressed to set the compression force (such as 5, 10 or 15 kilograms, etc.) of the elastic element 30 by the locking element 40. In use, when the tapping force is smaller than a preset compression force of the elastic element 30, the user may feel the tapping segment 22 generating an instant rebound, and when the tapping force is larger than the preset compression force of the elastic element 30, the user may feel the tapping segment 22 generating a delayed rebound. Therefore, the user can be reminded of the tapping force by identifying the compressed extent of the elastic element 30, and this may provide a force-limiting effect to the user.

Figure 4:
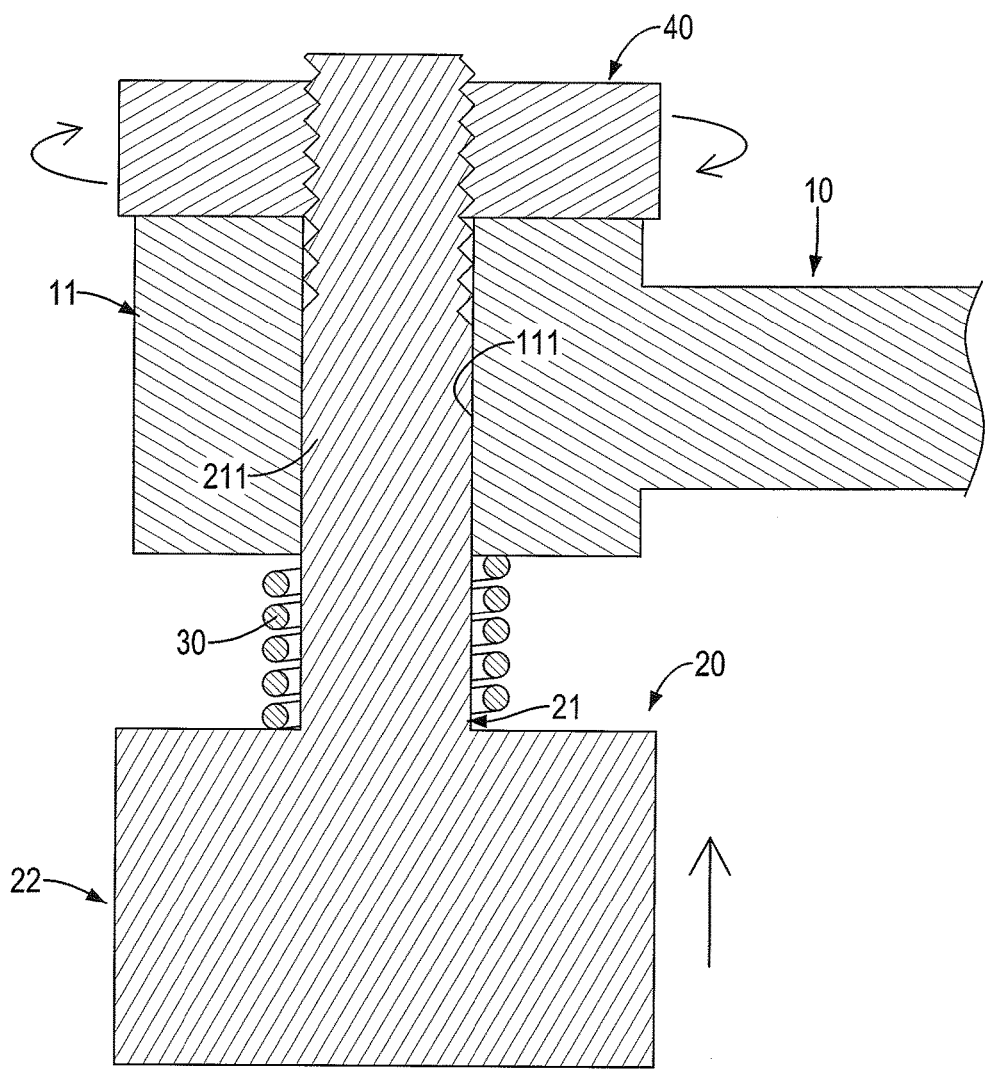
FIG. 4 is an enlarged and operational cross sectional side view of the force-limiting and damping device in FIG. 1.

The locking element 40 is connected to the mounting segment 21 of the tapping element 20, and abuts the connecting segment 11 of the body 10 to hold the elastic element 30 between the connecting segment 11 and the tapping segment 22. The structural relationship between the locking element 40 and the tapping element 20 may be a fixed structure or an adjustable structure. Further, the locking element 40 is disc-shaped and has a top side, a bottom side, and a locking hole 41. The locking hole 41 is formed through the top side and the bottom side of the locking element 40, aligns with the mounting hole 111 of the connecting segment 11, and is connected to the locking structure 211 of the mounting segment 21. Furthermore, the locking hole 41 has an inner thread screwed with the outer screw of the locking structure 211. With reference to FIGS. 3 and 4, a connecting position between the locking element 40 and the mounting segment 21 can be adjusted to change a distance between the tapping segment 22 and the connecting segment 11. Then, the compressed or expanded state of the elastic element 30 can be adjusted between the tapping segment 22 and the connecting segment 11.

Figure 5:
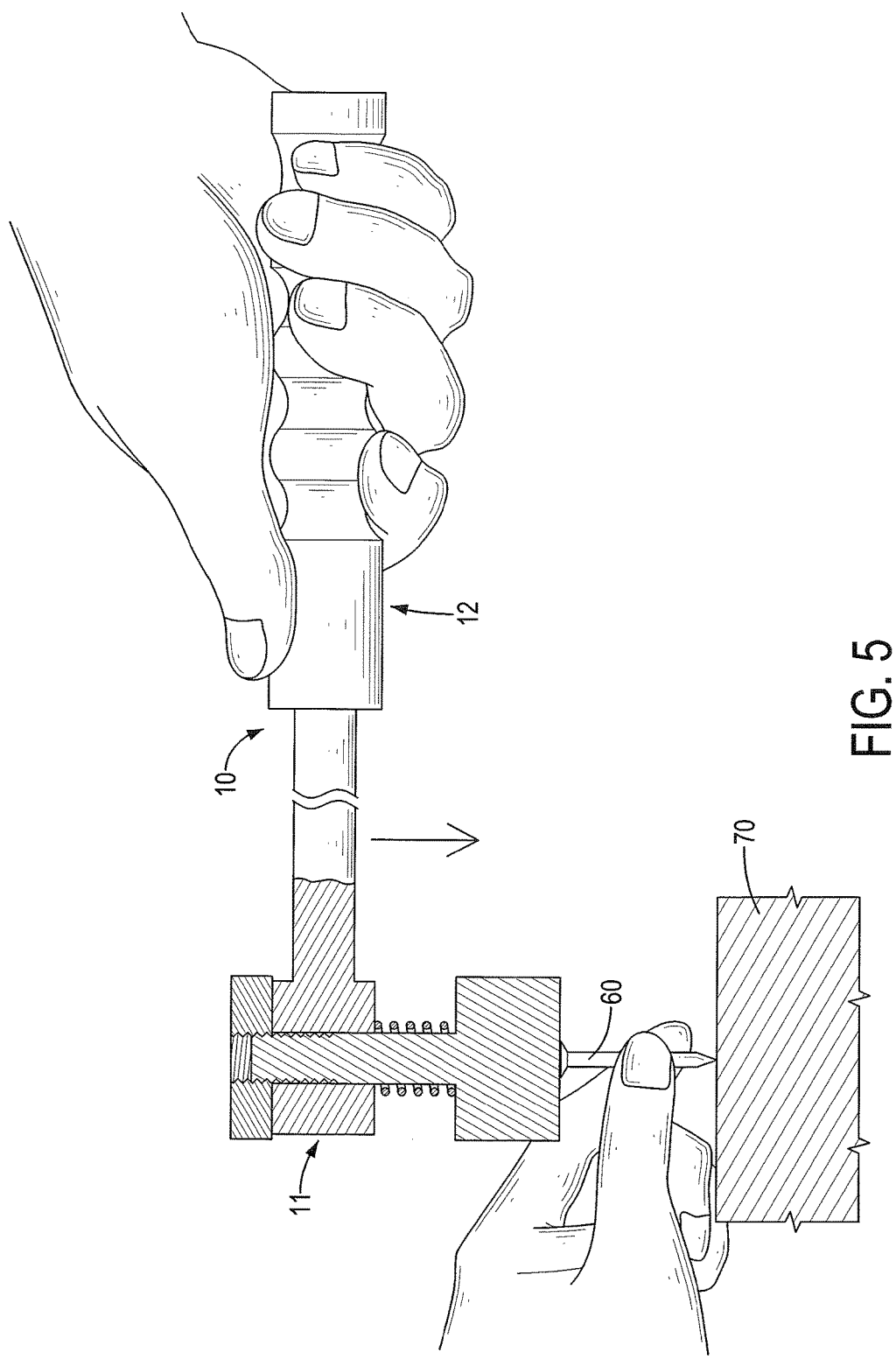
FIGS. 5 to 7 are operational side views of the force-limiting and damping device in FIG. 1, showing a nail tapped by the force-limiting and damping device.
Figure 6:
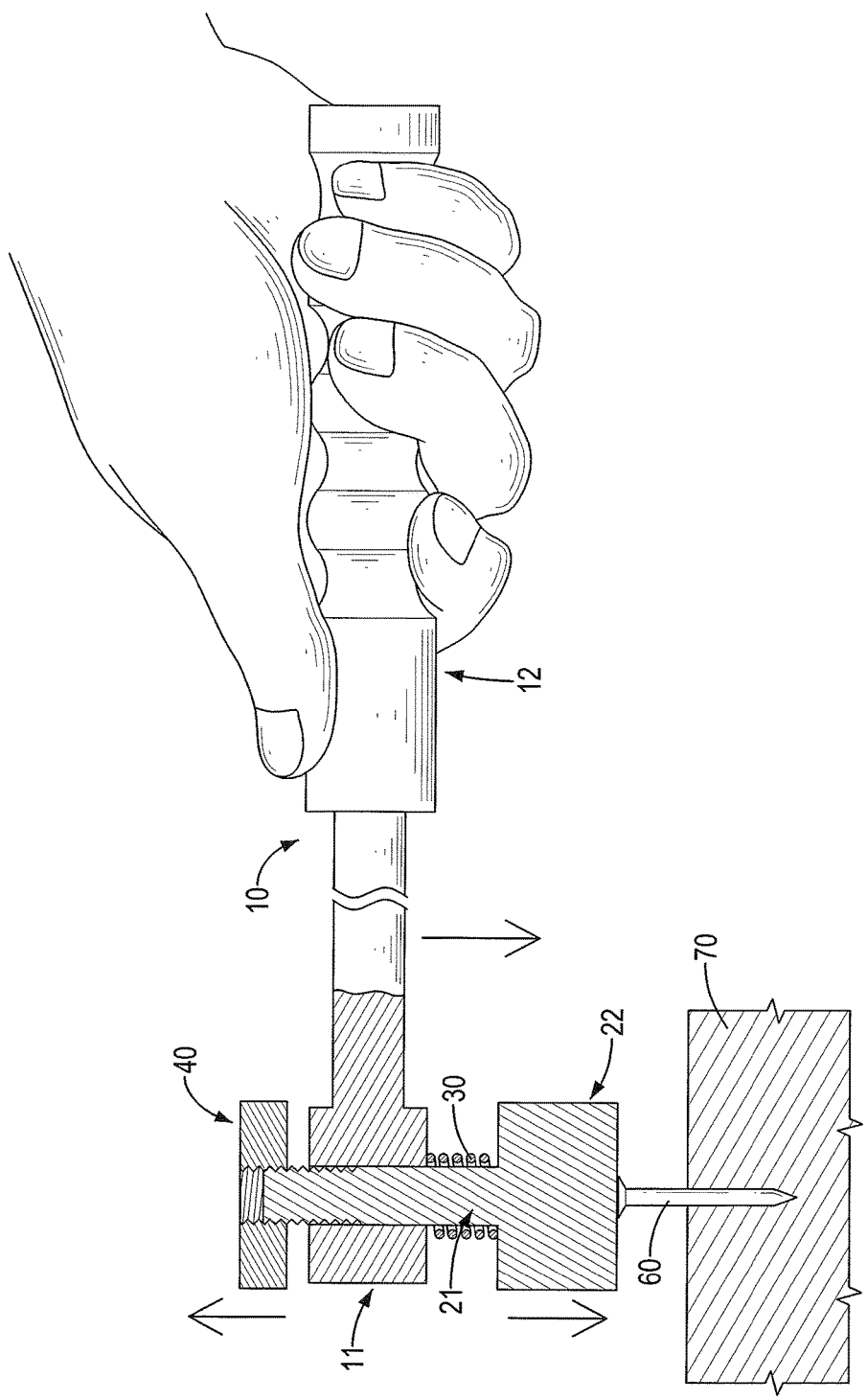
Figure 7:
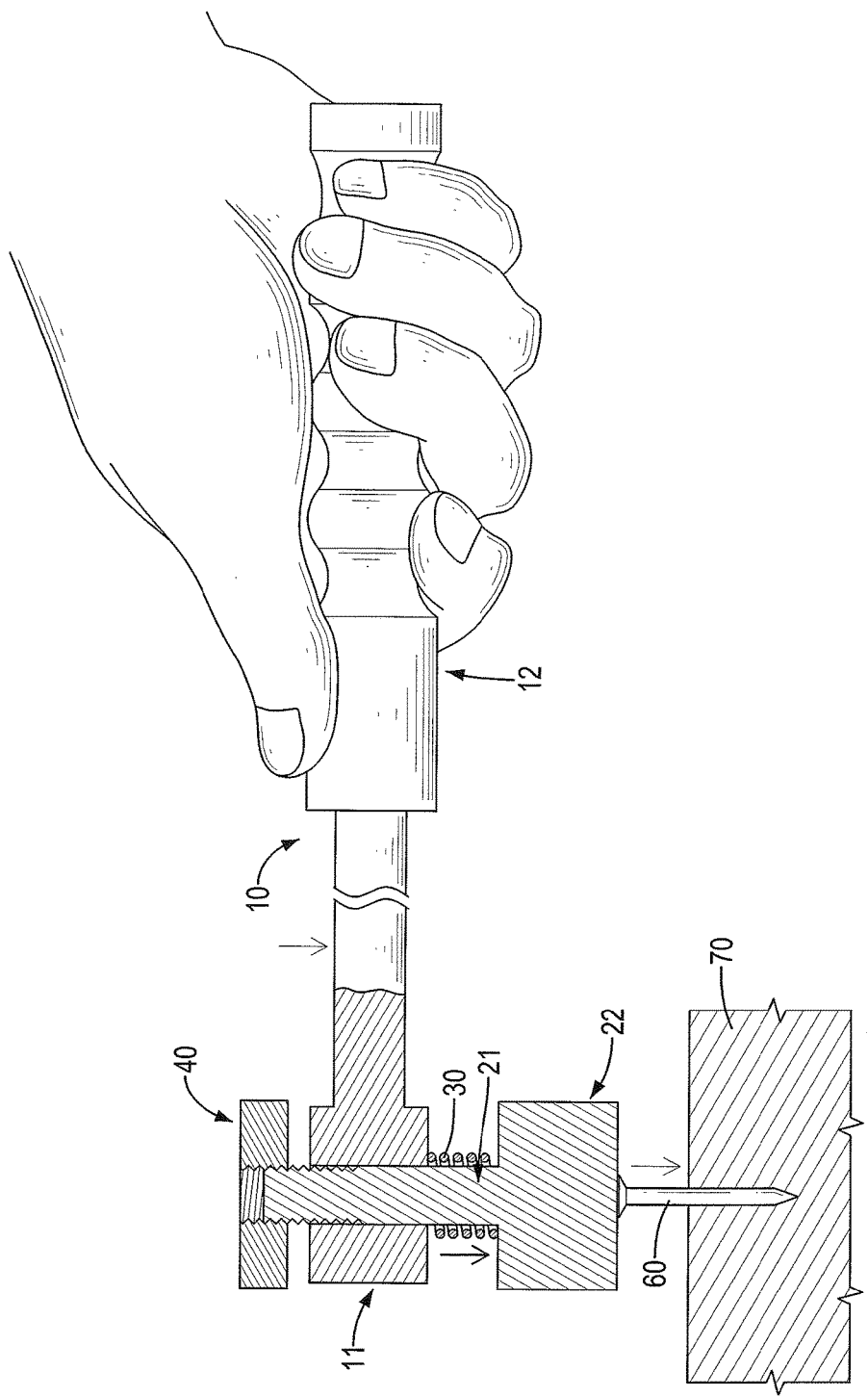

According to the above-mentioned structural relationship and features of the first embodiment of a force-limiting and damping device in accordance with the present invention, the force-limiting and damping device may be a medical hammer to tap a dental implant into a jaw patient's bones or an industrial hammer to tap a nail into a wooden board. With reference to FIGS. 5 to 7, when the industry hammer is used to tap a nail 60 into a wooden board 70, the user holds and moves the holding segment 12 of the body 10 to enable the tapping segment 22 of the tapping element 20 to hit against the nail 60. With further reference to FIG. 5, a reaction force is generated when the tapping segment 22 knocks against the nail 60. When the reaction force is smaller than the elastic force of the elastic element 30, the tapping face 221 of the tapping segment 22 will not move relative to the connecting segment 11, and the tapping segment 22 will receive an instant rebound reaction force.

With reference to FIG. 6, when the user applies a larger force to tap the nail 60 into the wooden board 70, the reaction force is larger than the elastic force of the elastic element 30, and the tapping segment 20 will move upwardly relative to the connecting segment 11 to compress the elastic element 30. Then, the tapping energy is transformed into the compressed potential energy of the elastic element 30. With reference to FIG. 7, the body 10 will be moved toward the nail 60 with the waving direction of the user (not going to rebound), and the potential energy of the elastic element 30 under the compressed state is released to enable the elastic element 30 to expand. When the elastic element 30 is expanded, the tapping segment 22 is pushed to move toward the nail 60, and this will increase the contacting time between the tapping face 221 of the tapping segment 22 and the nail 60.

By way of mounting the elastic element 30 between the connecting segment 11 and the tapping segment 22, a delayed rebound and damping effect is generated to the reaction force to prevent the industrial hammer from bouncing during the tapping process by an instant rebound reaction force. Then, the nail 60 will not bend or deflect easily, and the user's applied force is continuously transferred to the nail 60. This may reduce noise and the loss of energy. Furthermore, the user may only need to tap the nail 60 into the wooden board 70 several times, and this may reduce the numbers and time of tapping the nail 60 into the wooden board 70. Furthermore, when the force-limiting and damping device is a medical hammer, in use, the damping effect that is provided by the elastic element 30 may reduce the uncomfortable feeling of the user and the pain of the patient, and the user may hold the body 10 firmly to tap.

Furthermore, with reference to FIG. 2, the user may rotate the locking element 40 to separate from the mounting segment 21, and mount the elastic element 30 with different elastic forces between the connecting segment 11 and the tapping segment 22. Additionally, with reference to FIGS. 3 and 4, the distance between the connecting segment 11 and the tapping segment 22 is adjusted by rotating the locking element 40 to compress the elastic element 30 under a different compression status, and this may enable the elastic element 30 to have different elastic tensions.

According to the above-mentioned structural relationship and features of the first embodiment of a force-limiting and damping device in accordance with the present invention, the elastic element 30 between the connecting segment 11 and the tapping segment 22 may provide a damping and delayed rebound effect to the reaction force, increase the contacting time between the tapping face 221 of the tapping segment 22 and the nail 60 to prevent the nail 60 from bending or deflecting easily, reduce noise and the loss of energy, reduce the numbers and time of tapping the nail 60, reduce the uncomfortable feeling of the user and the pain of the patient, and enable the user to hold the body 10 firmly to tap. The structure of the force-limiting and damping device is simplified, and the elastic tension of the elastic element 30 can be adjusted by replacing the elastic element 30 with different elastic forces or rotating the locking element 40. Then, the force-limiting and damping device may provide a damping effect to a user, may provide a high stability in use and may be easily adjusted.

In addition, under the magnetic principle that like poles repel and unlike poles attract, a greatest magnetic attracting force is generated when two magnetic bodies are attracted to contact each other. When the two magnetic bodies are separated from each other, the magnetic attracting force disappears instantly. According to the magnetic principle, the connecting segment 11 and the locking element 40 are made of permanent magnets to enable the connecting segment 11 to attract the locking element 40. Since the magnetic field intensity of the permanent magnet is a fixed value and the elastic element 30 is selected with a weak elastic force without setting an internal tension, when the reaction force is generated by tapping and is larger than the magnetic attracting force between the connecting segment 11 and the locking element 40, the locking element 40 will separate from the connecting segment 11. Then, the magnetic attracting force between the connecting segment 11 and the locking element 40 will disappear. When the reaction force is smaller than the magnetic attracting force, the locking element 40 will not separate from the connecting segment 11, and the elastic element 30 only pushes the tapping segment 22 back to the original position. Therefore, the fixed value of the magnetic attracting force between the connecting segment 11 and the locking element 40 may provide an accurate limiting effect to the force-limiting and damping device.

Figure 8:
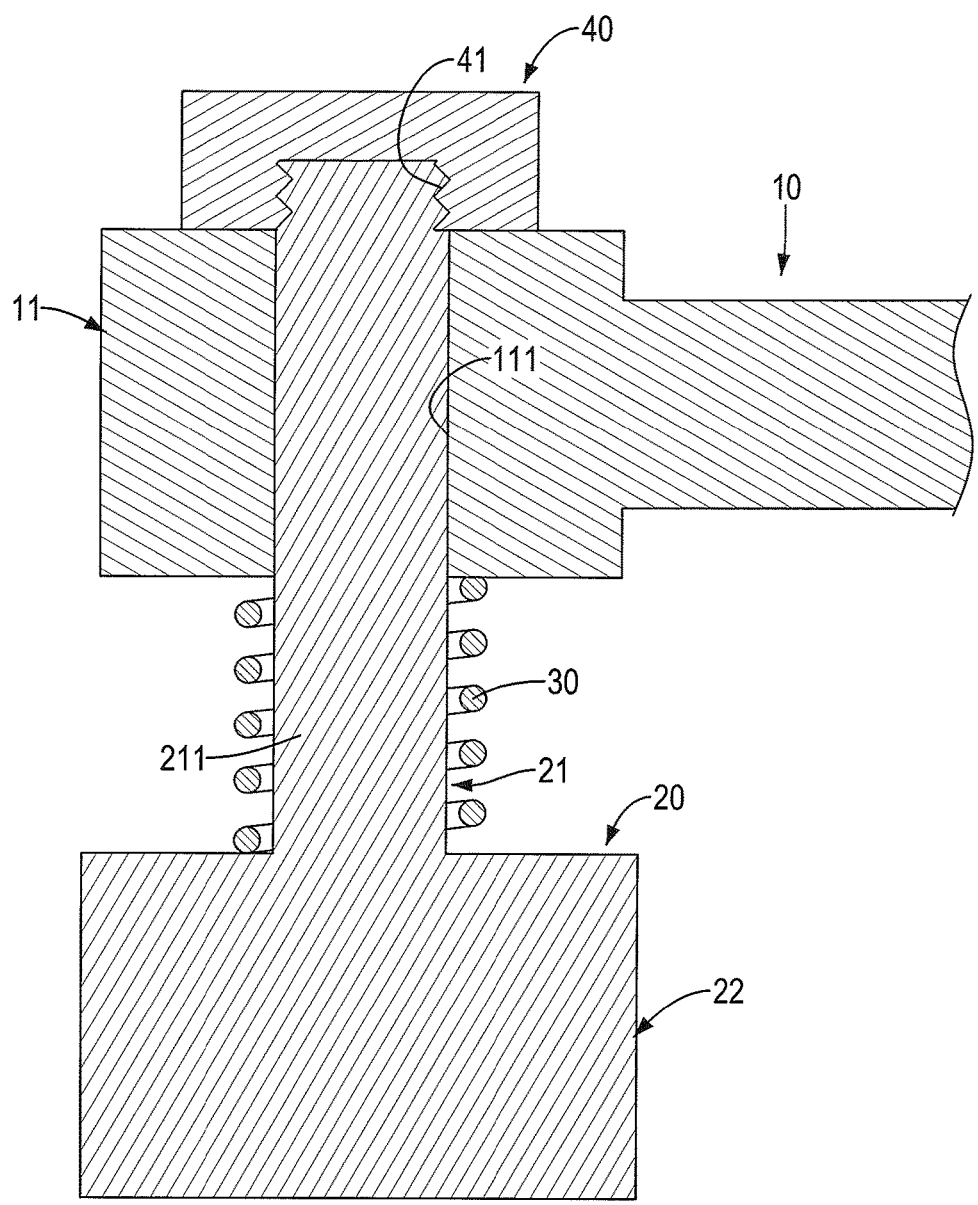
FIGS. 8 to 10 are cross sectional side views of the force-limiting and damping device in FIG. 1, with different shapes and structures.

Furthermore, the first embodiment of the force-limiting and damping device has other variable types. With reference to FIG. 8, the locking hole 41 of the locking element 40 is not formed through the top side of the locking element 40, and the position of the locking element 40 relative to the locking structure 211 of the mounting segment 21 is fixed. That is, the compression status of the elastic element 30 cannot be adjusted by rotating the locking element 40. A fixed elastic force of the elastic element 30 can be used in the force-limiting and damping device.

Figure 9:
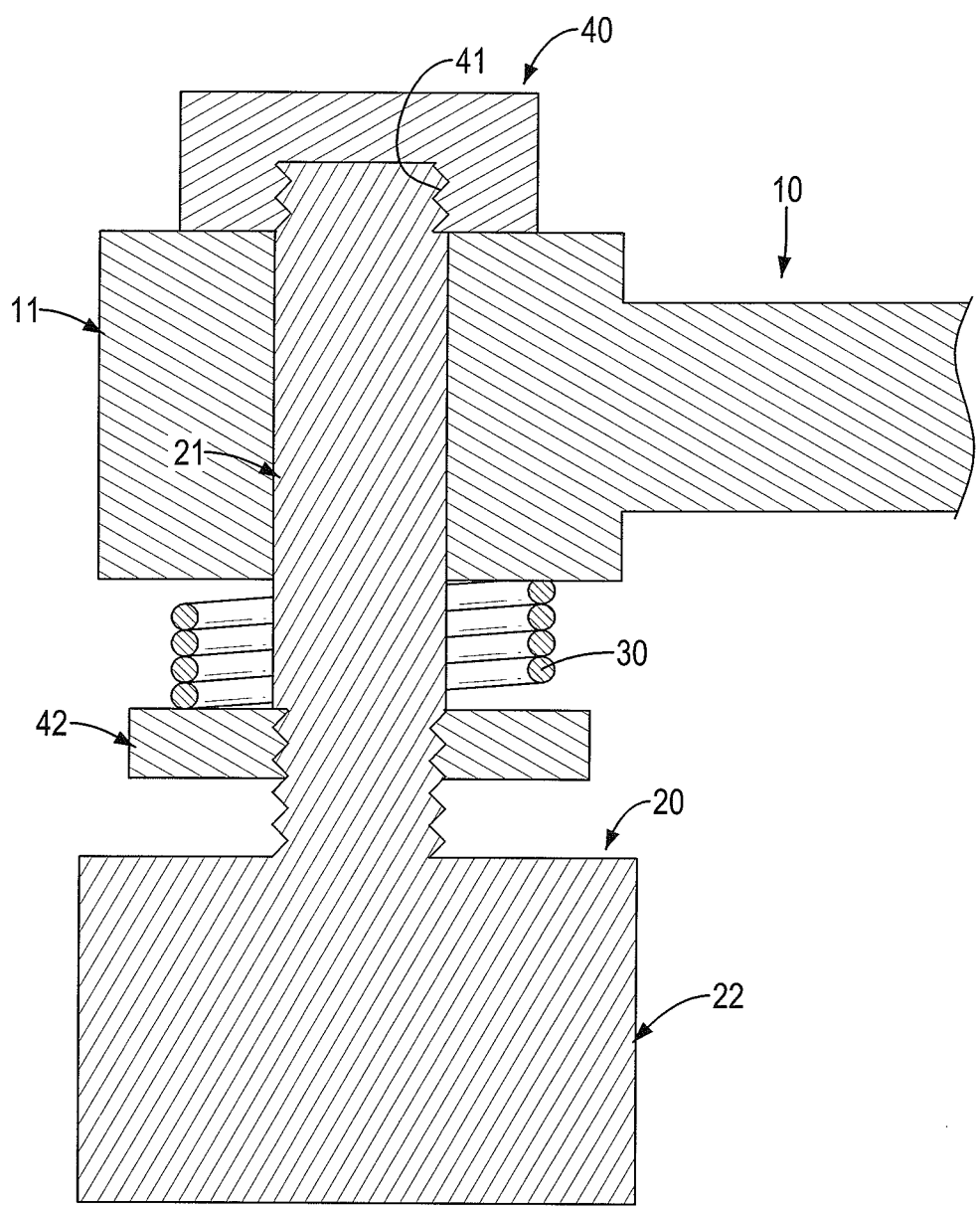

With reference to FIG. 9, when using the locking element 40 as shown in FIG. 8, the elastic force of the elastic element 30 can be adjusted by mounting an adjusting ring 42 rotatably on the mounting segment 21 between the elastic element 30 and the tapping segment 22. That is, the elastic element 30 is mounted around the mounting segment 21 between the connecting segment 11 and the adjusting ring 42. Then, the user may rotate the adjusting ring 42 to adjust a distance between the adjusting ring 42 and the connecting segment 11, and the compression status of the elastic element 30 can be adjusted to provide different elastic forces.

Figure 10:
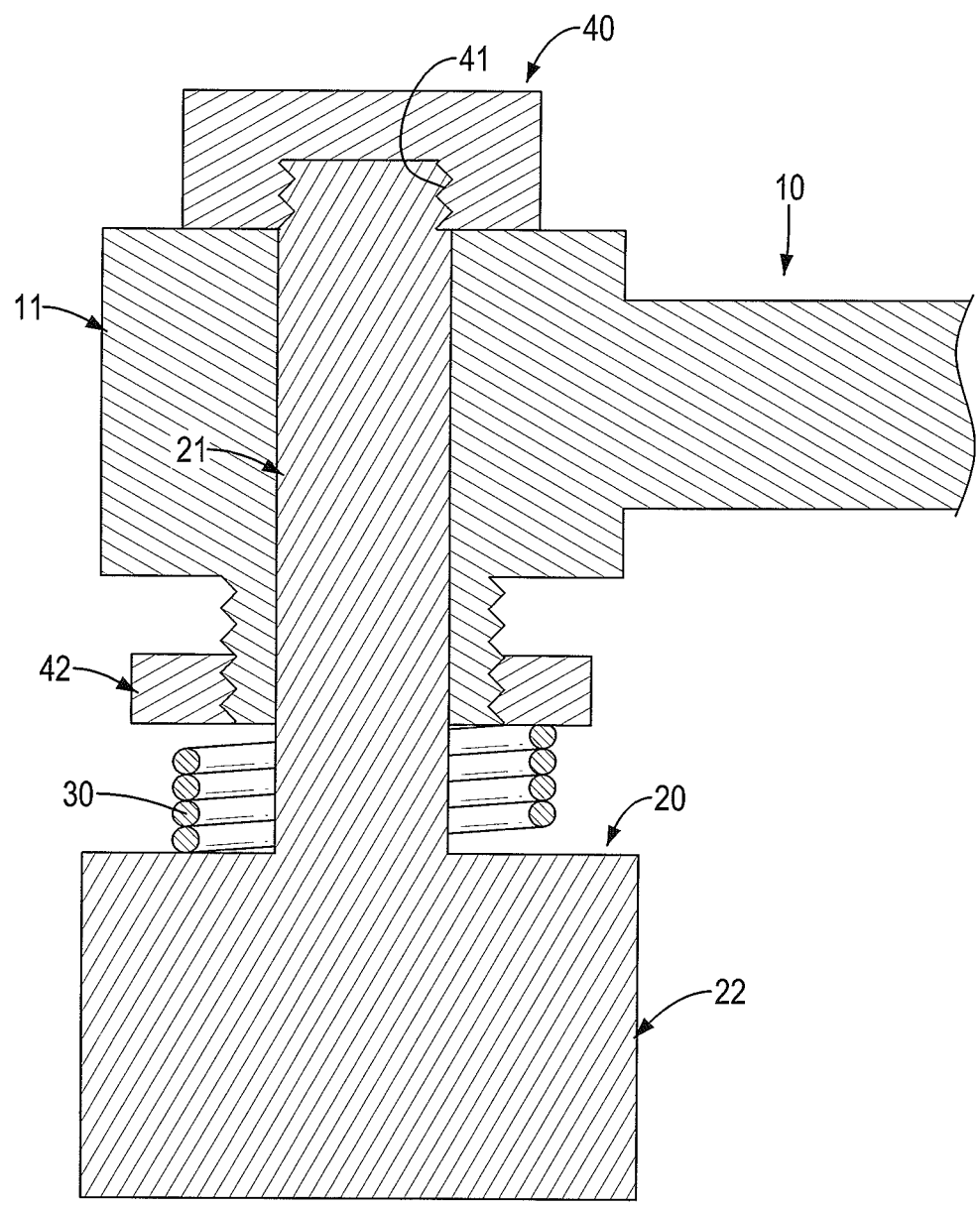

Additionally, with reference to FIG. 10, the adjusting ring 42 may be rotatably mounted on a bottom portion of the connecting segment 11 between the elastic element 30 and the connecting segment 11. That is, the elastic element 30 is mounted around the mounting segment 21 between the tapping segment 22 and the adjusting ring 42. Then, the user also can adjust a distance between the tapping segment 22 and the adjusting ring 42 by rotating the adjusting ring 42, and this may change the compression status of the elastic element 30 to enable the elastic element 30 to have different elastic forces.

Figure 11:
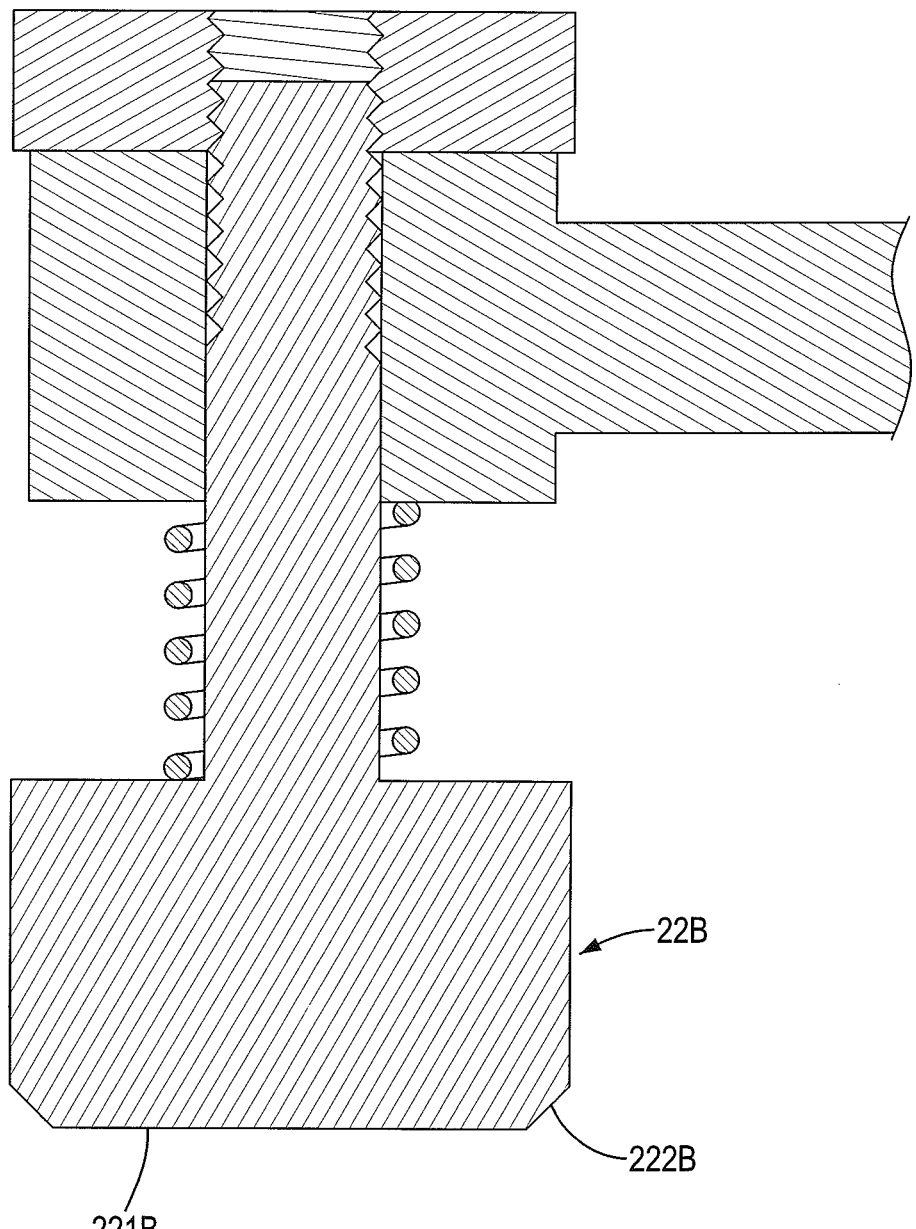
FIG. 11 is an enlarged cross sectional side view of a second embodiment of a force-limiting and damping device in accordance with the present invention.

With reference to FIG. 11, a second embodiment of a force-limiting and damping device in accordance with the present invention is substantially the same as the first embodiment except for the following features. The tapping segment 22B has an external surface and a chamfered face 222B. The chamfered face 222B is annularly formed on the external surface of the tapping segment 22B adjacent to the tapping face 221B of the tapping segment 22B. In use, when the tapping segment 22B is knocked against the nail 60 and a contact point between the tapping segment 22B and when the nail 60 is close to an edge of the tapping face 221B, the chamfered face 222B may provide a vertical component force and a horizontal component force to the nail 60 at the same time, and this may reduce the torsion force that may deform the nail 60. Then, the nail 60 may be tapped into the wooden board 70 stably.

Figure 12:
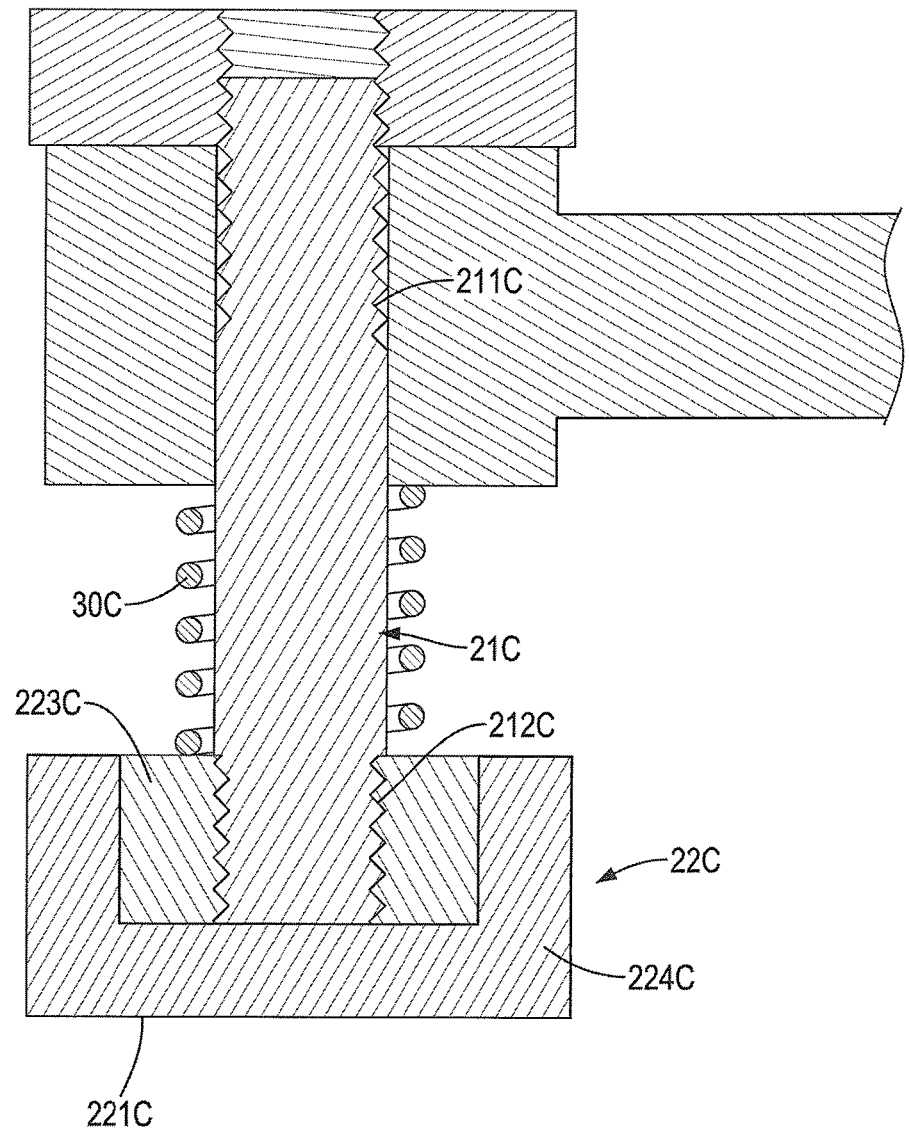
FIG. 12 is an enlarged cross sectional side view of a third embodiment of a force-limiting and damping device in accordance with the present invention.

With reference to FIG. 12, a third embodiment of a force-limiting and damping device in accordance with the present invention is substantially the same as the first embodiment except for the following features. The tapping segment 22C is not formed with the mounting segment 21C, and the mounting segment 21C has a threaded section 212C formed on the external surface of the mounting segment 21C adjacent to the forming end of the mounting segment 21C and being opposite the locking structure 211C.

The tapping segment 22C has a fixed ring 223C and a tapping cap 224C. The fixed ring 223C is securely connected to the threaded section 212C of the mounting segment 21C and abuts the elastic element 30C. Furthermore, the fixed ring 223C may be a nut. The tapping cap 224C is securely mounted around the fixed ring 223C at a bottom portion of the tapping element 20C, and the tapping face 221C of the tapping segment 22C is formed on a bottom of the tapping cap 224C. Additionally, the tapping cap 224C is made of rubber or silicone, and the tapping face 221C that is made of elastic material may be used in a combining process of tapped objects such as tiles or wood that are not allowed to have any damage. In addition, the threaded section 212C may be axially formed in the forming end of the mounting segment 21C opposite the locking structure 211C, the fixed ring 223C is connected to the threaded section 212C, and the tapping cap 224C may be an annular ring and is connected to the fixed ring 223C. Further, the fixed ring 223C may be formed with the mounting segment 21C as a single piece, and the tapping cap 224C is a cap made of rubber or silicone and is directly mounted around the fixed ring 223C.

Figure 13:
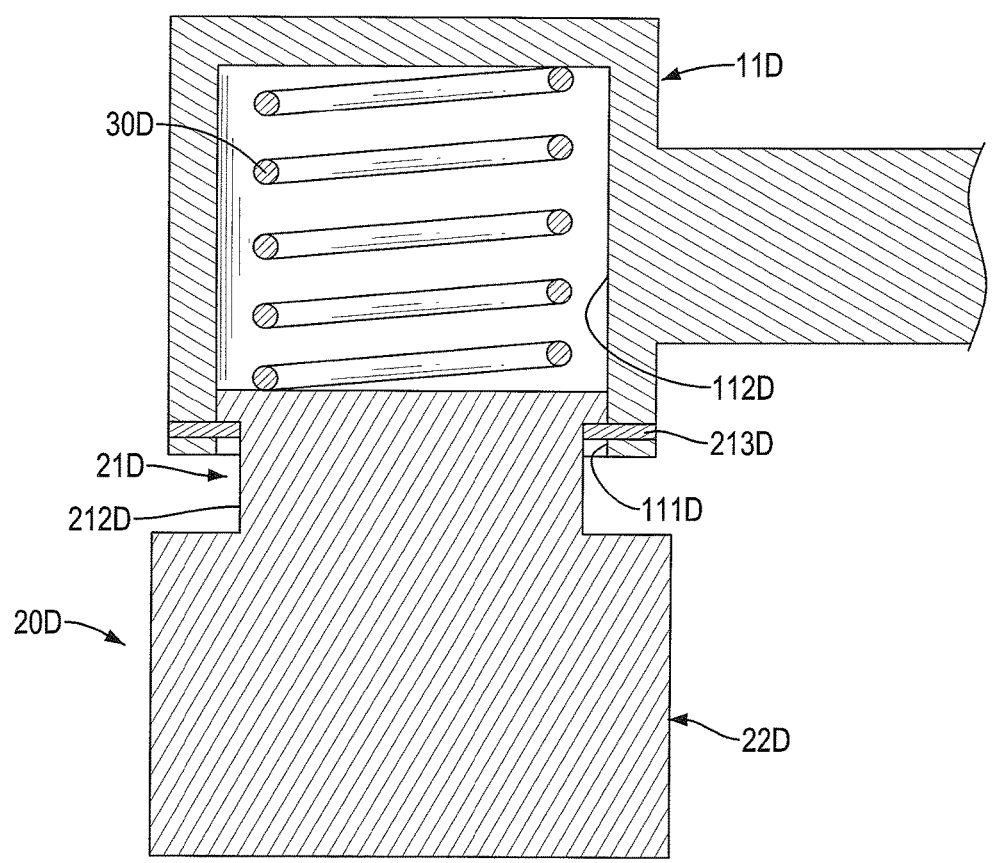
FIG. 13 is an enlarged cross sectional side view of a fourth embodiment of a force-limiting and damping device in accordance with the present invention.

With reference to FIG. 13, a fourth embodiment of a force-limiting and damping device in accordance with the present invention is substantially the same as the first embodiment except for the following features. The mounting hole 111D is not formed through the top side of the connecting segment 11D to form a chamber 112D in the connecting segment 11D and communicating with the mounting hole 111D. The mounting segment 21D of the tapping element 20D is movably mounted in the connecting segment 11D via the mounting hole 111D, and the elastic element 30D is mounted in the chamber 112D of the connecting segment 11D and abuts the mounting segment 21D of the tapping element 20D to enable the elastic element 30D to mount between the connecting segment 11D and the mounting segment 21D.

Furthermore, the force-limiting and damping device of the fourth embodiment does not have the locking element 40. The mounting segment 21D further has a limiting recess 212D and at least one positioning pin 213D. The limiting recess 212D is annularly formed in the external surface of the mounting segment 21D and communicates with the chamber 112D. The at least one positioning pin 213D is transversally mounted through the external surface of the connecting segment 11D and extends into the limiting recess 212D to hold the mounting segment 21D with the connecting segment 11D. Additionally, when the force-limiting and damping device is a medical or surgical hammer, the weight of the force-limiting and damping device should be considered, and the force-limiting and damping device should not rust in the sterilization process, so that the elastic force of the elastic element 30D will not change under repeated sterilization. Thus, the force-limiting and damping device can be cleaned, disinfected and used easily.

Figure 14:
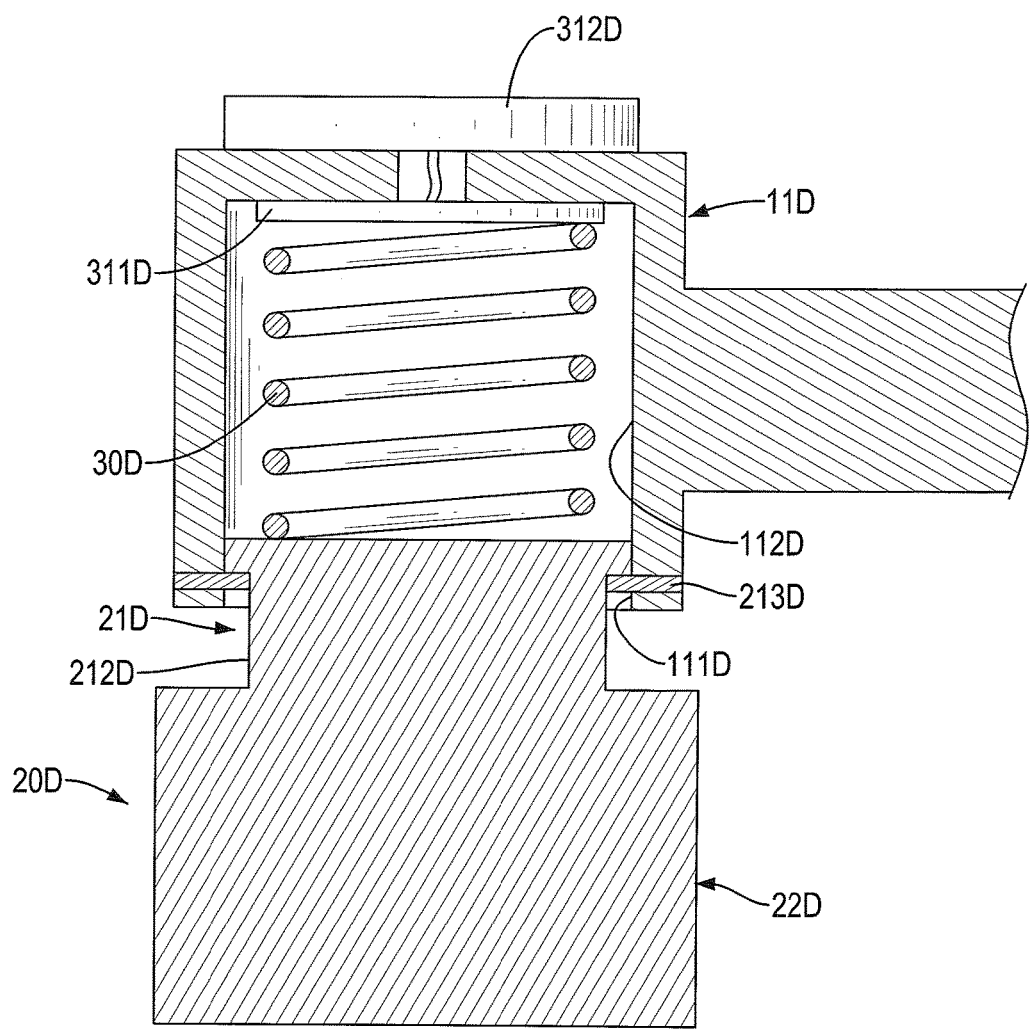
FIG. 14 is an enlarged cross sectional side view of a fifth embodiment of a force-limiting and damping device in accordance with the present invention.

With reference to FIG. 14, a fifth embodiment of a force-limiting and damping device in accordance with the present invention is substantially the same as the fourth embodiment except for the following features. The elastic element 30D further has a pressure type sensor 311D and a display 312D. The sensor 311D is mounted in the chamber 112D of the connecting segment 11D and abuts the elastic element 30D. The display 312D is securely mounted on the top side of the connecting segment 11D and is electrically connected to the sensor 311D. When the elastic element 30D is compressed by the tapping element 20D, the sensor 311D may detect the tapping force of the tapping element 20D via the compression force of the elastic element 30D, and the detected tapping force of the tapping element 20D may be shown on the display 312D. This may provide a tapping reference to the user.

Figure 15:
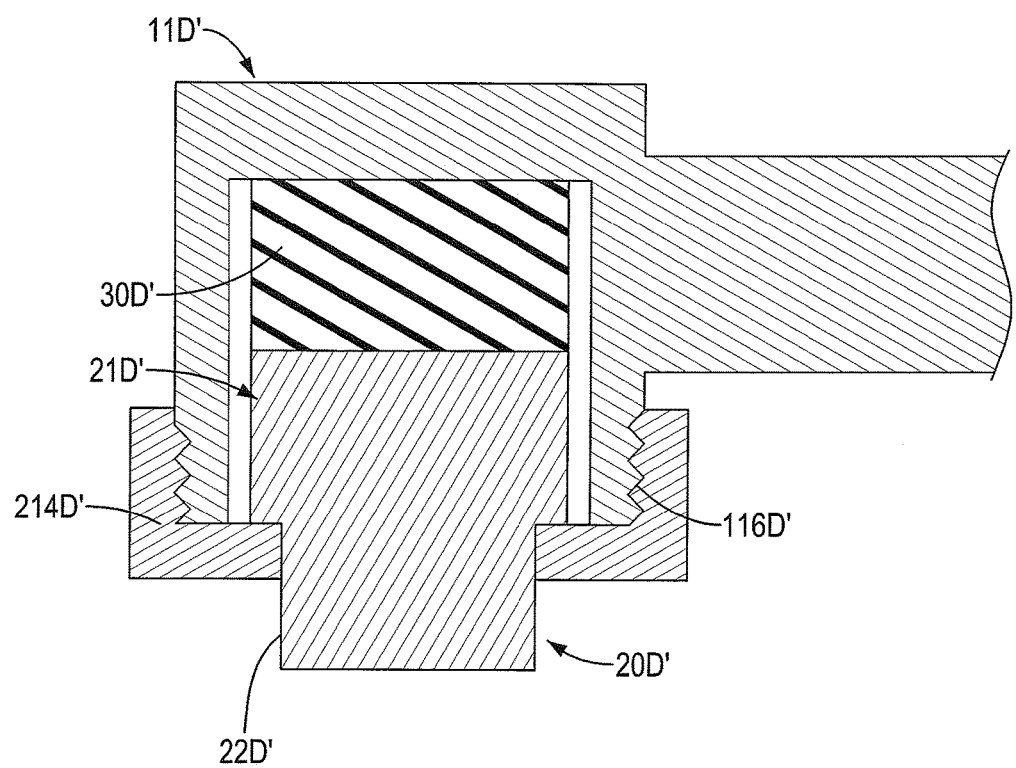
FIG. 15 is an enlarged cross sectional side view of a sixth embodiment of a force-limiting and damping device in accordance with the present invention.

With reference to FIG. 15, a sixth embodiment of a force-limiting and damping device in accordance with the present invention is substantially the same as the fifth embodiment except for the following features. The connecting segment 11D' has an outer thread 116D' formed on the external surface of the connecting segment 11D' adjacent to the bottom side of the connecting segment 11D'. The mounting segment 21D' has a limiting cover 214D' connected to the outer thread 116D' of the connecting segment 11D' to enable the tapping segment 22D' of tapping element 20D' to extend out of the bottom side of the connecting segment 11D' via the limiting cover 214D'. The elastic element 30D' is mounted in the connecting segment 11D', abuts the mounting segment 21D' and may be made of rubber, silicone, a flexible metal block or a flexible block.

Figure 16:
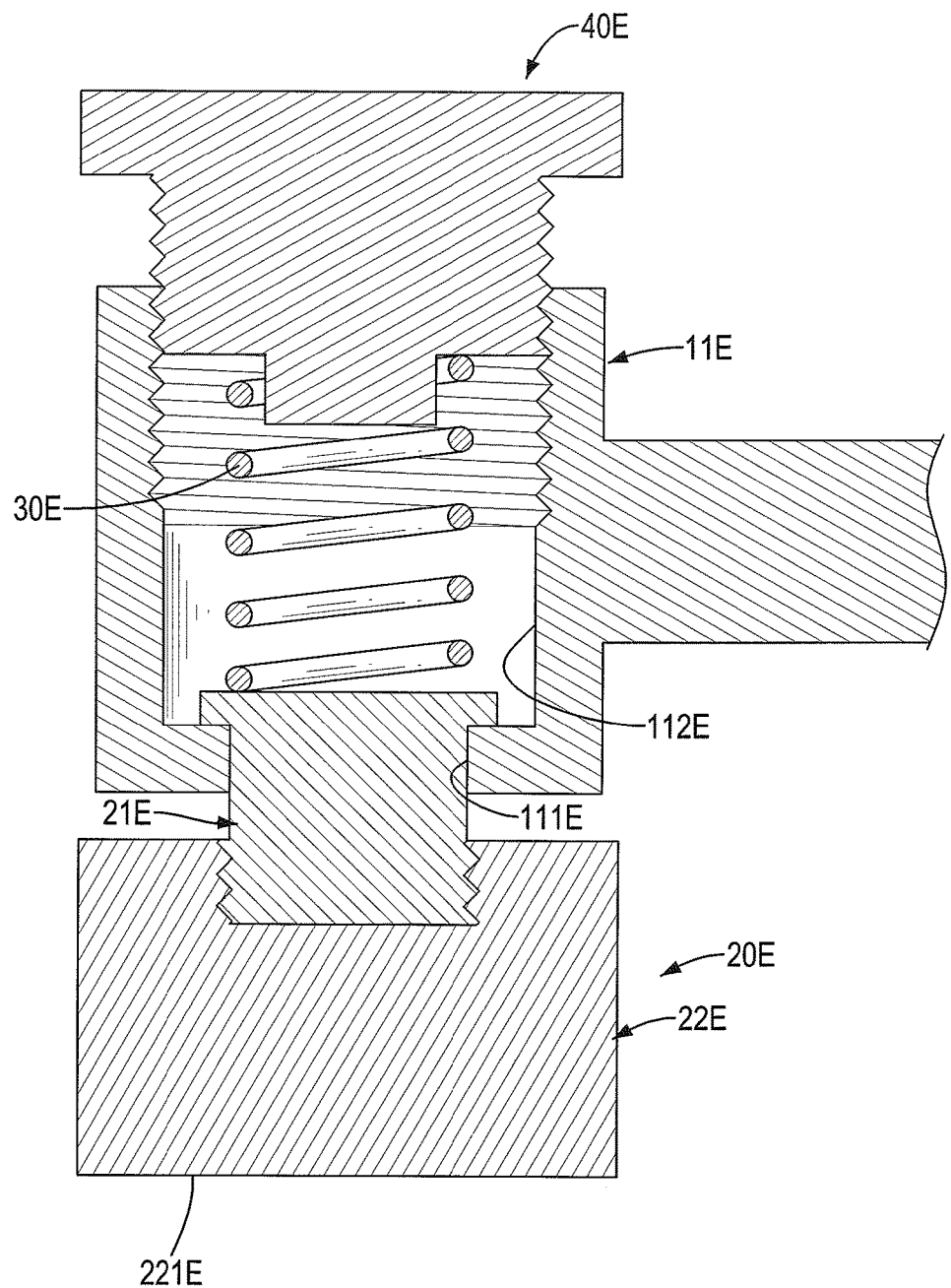
FIG. 16 is an enlarged cross sectional side view of a seventh embodiment of a force-limiting and damping device in accordance with the present invention.

With reference to FIG. 16, a seventh embodiment of a force-limiting and damping device in accordance with the present invention is substantially the same as the fifth embodiment except for the following features. The mounting hole 111E is formed through the top side and the bottom side of the connecting segment 11E and communicates with the chamber 112E. The tapping segment 22E of tapping element 20D' is connected to the mounting segment 21E by screwing without forming as a single piece. Furthermore, the mounting hole 111E has two inner diameters, with one of the inner diameters of the mounting hole 111E formed at the top side of the connecting segment 11E and wider than the other inner diameter that is formed at the bottom side of the connecting segment 11E.

Then, the mounting segment 21E is mounted in the chamber 112E of the connecting segment 11E via the mounting hole 111E at the top side of the connecting segment 11E, and extends out of the bottom side of the connecting segment 11E via the mounting hole 111E at the bottom side of the connecting segment 11E. The tapping segment 22E is connected to the mounting segment 21E that extends out of the connecting segment 11E. The locking element 40E is rotatably connected to the top side of the connecting segment 11E and extends into the chamber 112E. The elastic element 30E is mounted in the chamber 112E of the connecting segment 11E and abuts the mounting segment 21E and the locking element 40E. Then, the user may rotate the locking element 40E to move relative to the connecting segment 11E to apply adjustable pressure to the elastic element 30E, and this may enable the elastic element 30E to compress or expand.

Figure 17:
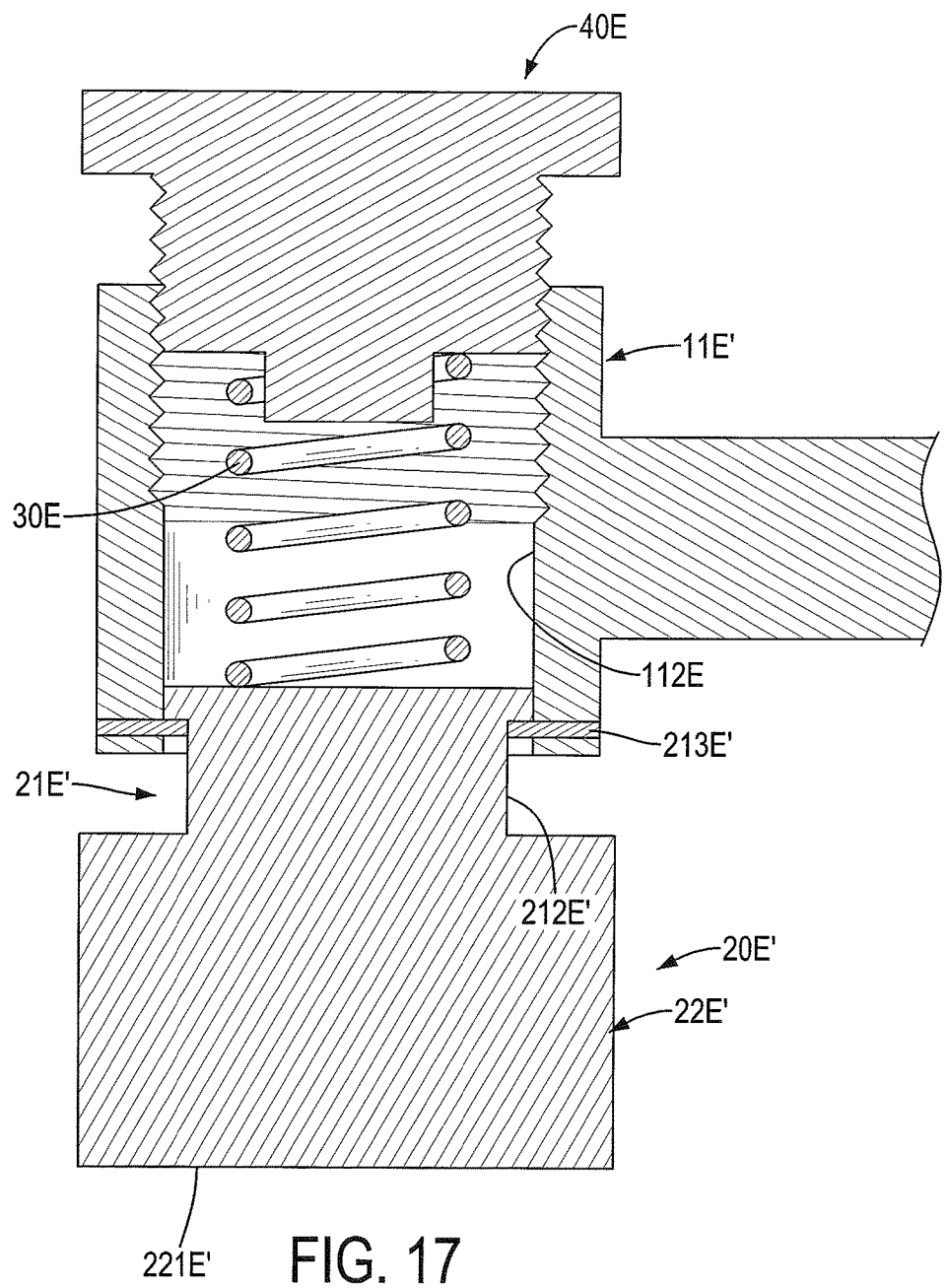
FIG. 17 is an enlarged cross sectional side view of an eighth embodiment of a force-limiting and damping device in accordance with the present invention.

With reference to FIG. 17, an eighth embodiment of a force-limiting and damping device in accordance with the present invention is substantially the same as the seventh embodiment except for the following features. The mounting segment 21E' of the tapping element 20E' is formed with the tapping segment 22E' as a single piece, and has a limiting recess 212E' and at least one positioning pin 213E'. The limiting recess 212E' is annularly formed in the external surface of the mounting segment 21E', and the at least one positioning pin 213E' is transversally mounted through the external surface of the connecting segment 11E' and extends into the limiting recess 212E' to hold the mounting segment 21E' with the connecting segment 11E'.

Figure 18:
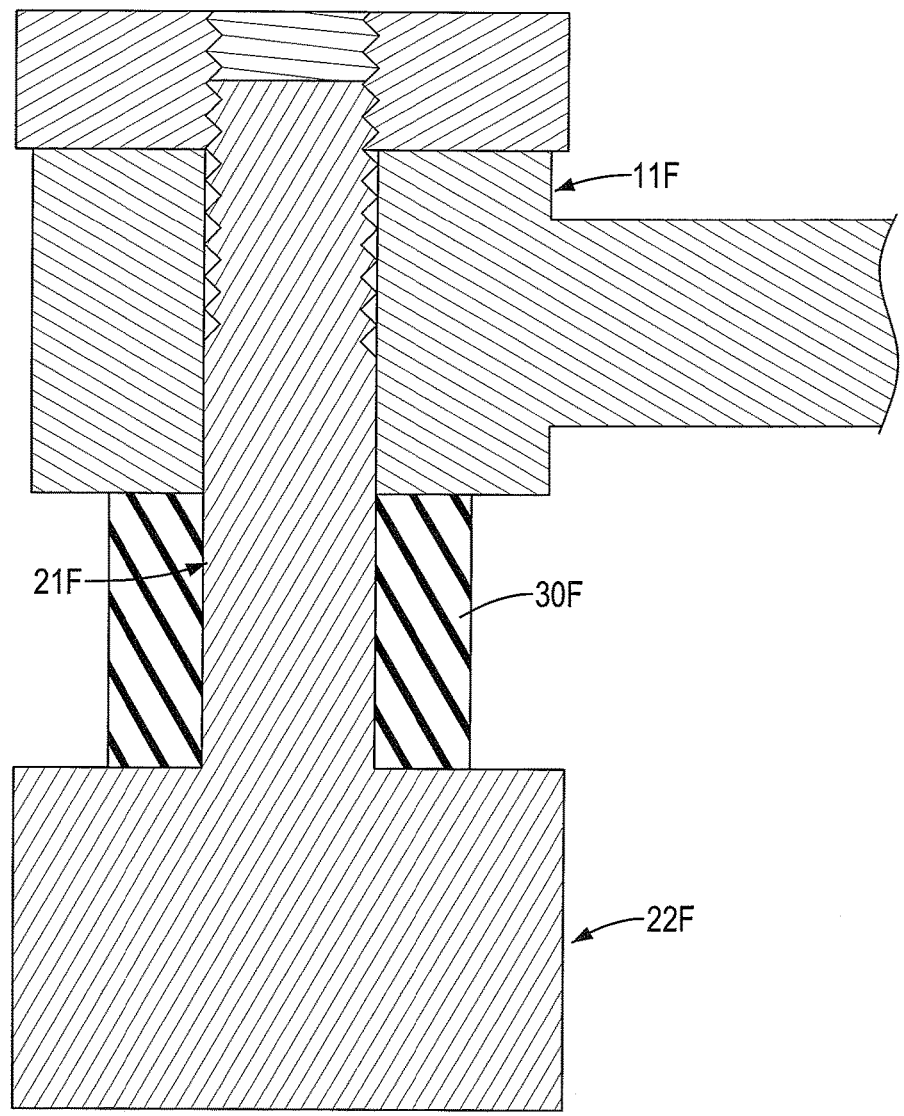
FIG. 18 is an enlarged cross sectional side view of a ninth embodiment of a force-limiting and damping device in accordance with the present invention.

With reference to FIG. 18, a ninth embodiment of a force-limiting and damping device in accordance with the present invention is substantially the same as the first embodiment except for the following features. The elastic element 30F is an annular rubber or silicone, a flexible metal block or a flexible block, and is mounted around the mounting segment 21F between the connecting segment 11F and the tapping segment 22F.

Figure 19:
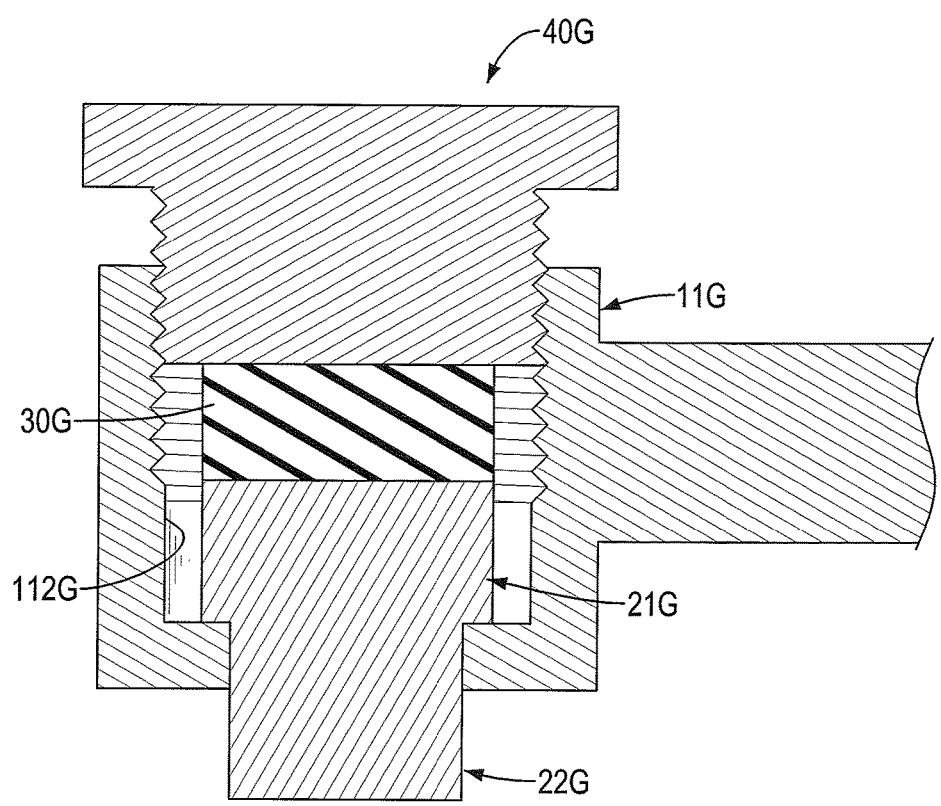
FIG. 19 is an enlarged cross sectional side view of a tenth embodiment of a force-limiting and damping device in accordance with the present invention.

With reference to FIG. 19, a tenth embodiment of a force-limiting and damping device in accordance with the present invention is substantially the same as the seventh embodiment except for the following features. The mounting segment 21G is formed with the tapping segment 22G as a single piece. The elastic element 30G is a rubber block, a silicone block, a flexible metal block or a flexible block, and is mounted in the chamber 112G of the connecting segment 11G between the mounting segment 21G and the locking element 40G. Additionally, the tapping element 20E and the elastic element 30E in the seventh embodiment can be used with the mounting segment 21G the tapping segment 22G, and the elastic element 30G in the tenth embodiment.

Figure 20:
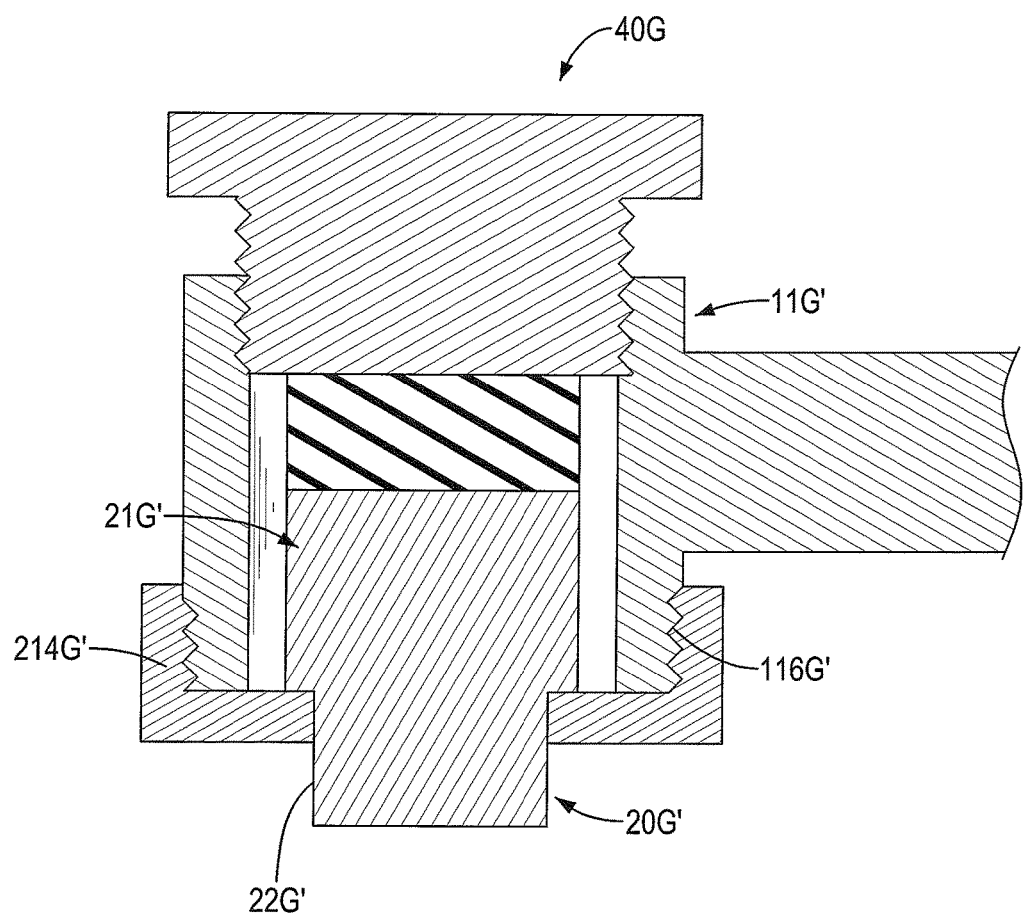
FIG. 20 is an enlarged cross sectional side view of an eleventh embodiment of a force-limiting and damping device in accordance with the present invention.

With reference to FIG. 20, an eleventh embodiment of a force-limiting and damping device in accordance with the present invention is substantially the same as the tenth embodiment except for the following features. The connecting segment 11G' has an outer thread 116G' formed on the external surface of the connecting segment 11G' adjacent to the bottom side of the connecting segment 11G'. The mounting segment 21G' has a limiting cover 214G' connected to the outer thread 116G' of the connecting segment 11G' to enable the tapping segment 22G' of tapping element 20G' to extend out of the bottom side of the connecting segment 11G' via the limiting cover 214G'.

Figure 21:
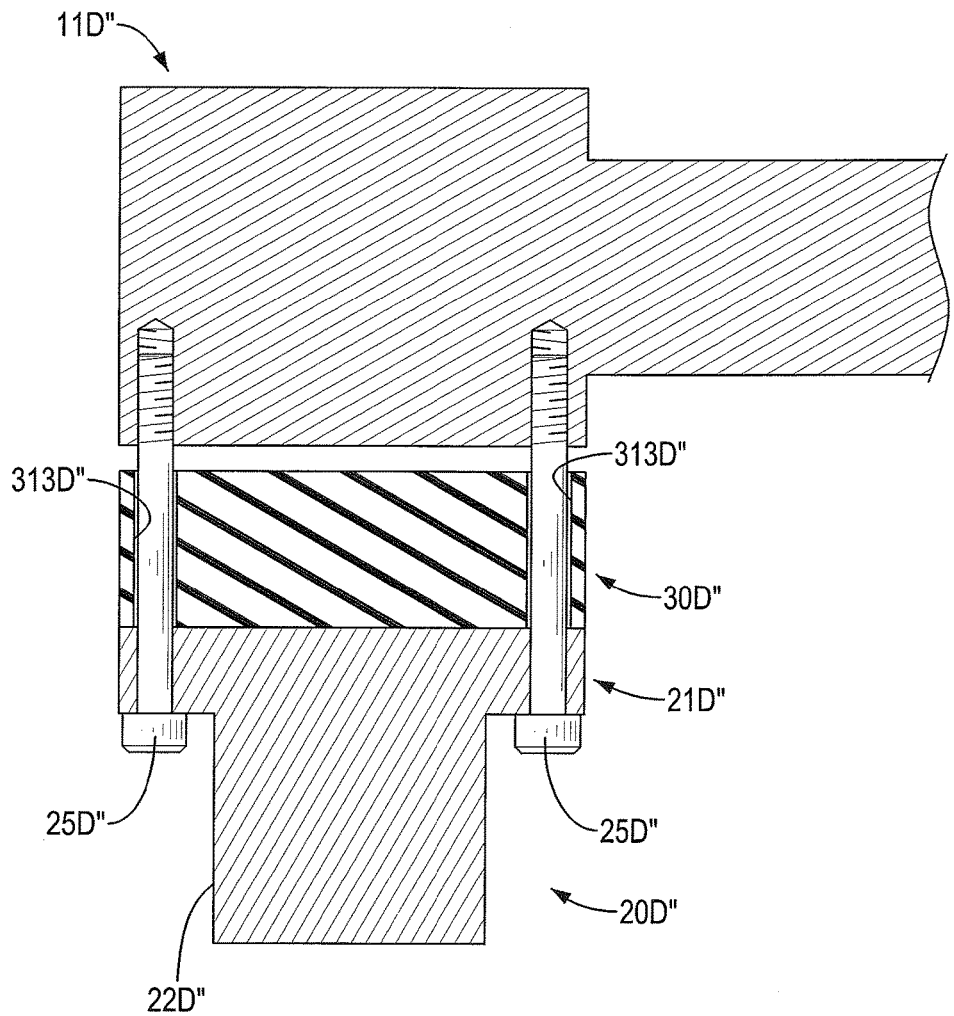
FIG. 21 is an enlarged cross sectional side view of a twelfth embodiment of a force-limiting and damping device in accordance with the present invention.

With reference to FIG. 21, a twelfth embodiment of a force-limiting and damping device in accordance with the present invention is substantially the same as the first embodiment except for the following features. The connecting segment 11D" is a solid structure, and the tapping element 20D" has multiple limiting rods 25D" longitudinally mounted through the mounting segment 21D" and connected to the connecting segment 11D" to hold the tapping segment 22D" below the connecting segment 11D". The elastic element 30D" is mounted between the connecting segment 11D" and the mounting segment 21D" and has multiple through holes 313D" formed through the elastic element 30D" to enable the limiting rods 25D" to mount through the elastic element 30D".

Figure 22:
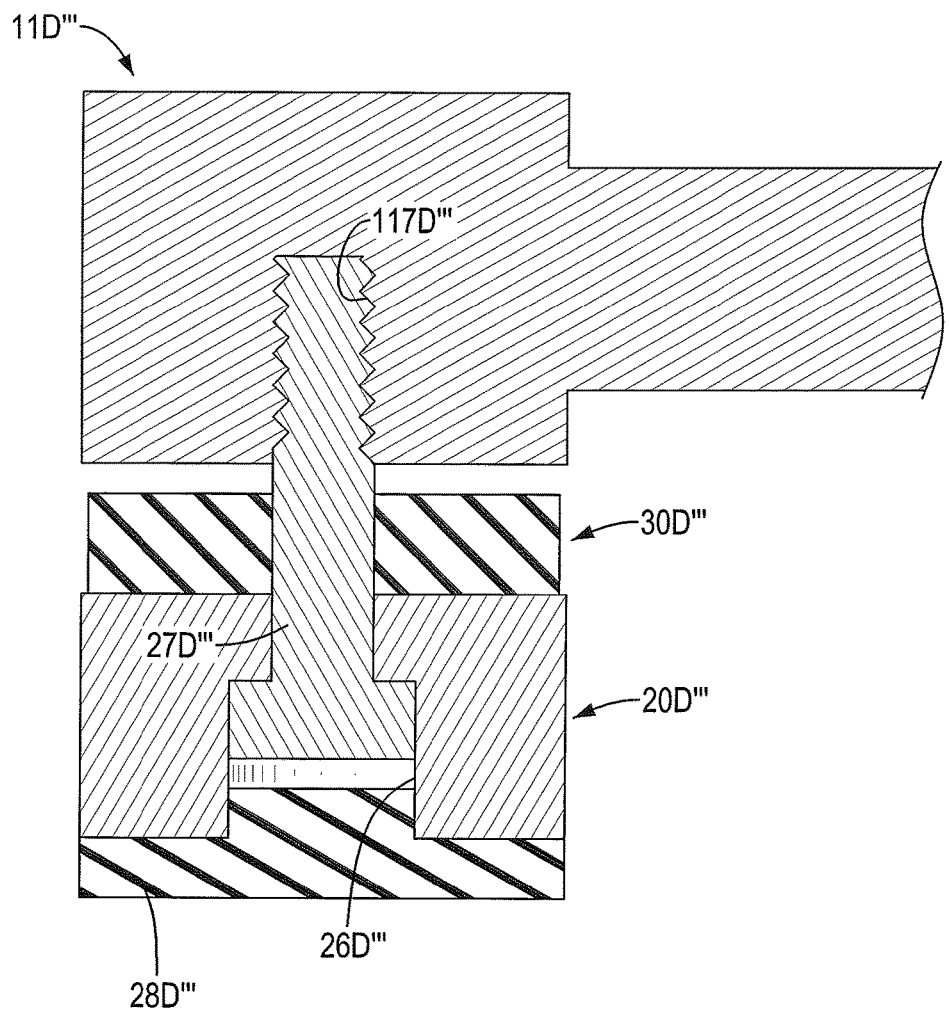
FIG. 22 is an enlarged cross sectional side view of a thirteenth embodiment of a force-limiting and damping device in accordance with the present invention.

With reference to FIG. 22, in a thirteenth embodiment of a force-limiting and damping device in accordance with the present invention, the connecting segment 11D''' has a connecting hole 117D''' formed in the bottom side of the connecting segment 11D''', and the tapping element 20D''' has an engaging through hole 26D''' and a connecting rod 27D'''. The engaging through hole 26D''' is stepped and is longitudinally formed through the tapping element 20D''', and the connecting rod 27D''' is mounted through the engaging through hole 26D''' and is securely mounted in the connecting hole 117D''' to connect the tapping element 20D''' with the connecting segment 11D'''. The elastic element 30D''' is mounted around the connecting rod 27D''' between the connecting segment 11D''' and the tapping element 20D'''. Further, the tapping element 20D''' has a tapping board 28D''' mounted on a bottom of the tapping element 20D''' to cover the engaging through hole 26D'''. The tapping board 28D''' may be made of metal, polyethylene (PE), hard material such as plastic, or elastic materials such as rubber, silicone, wood or leather.

Figure 23:
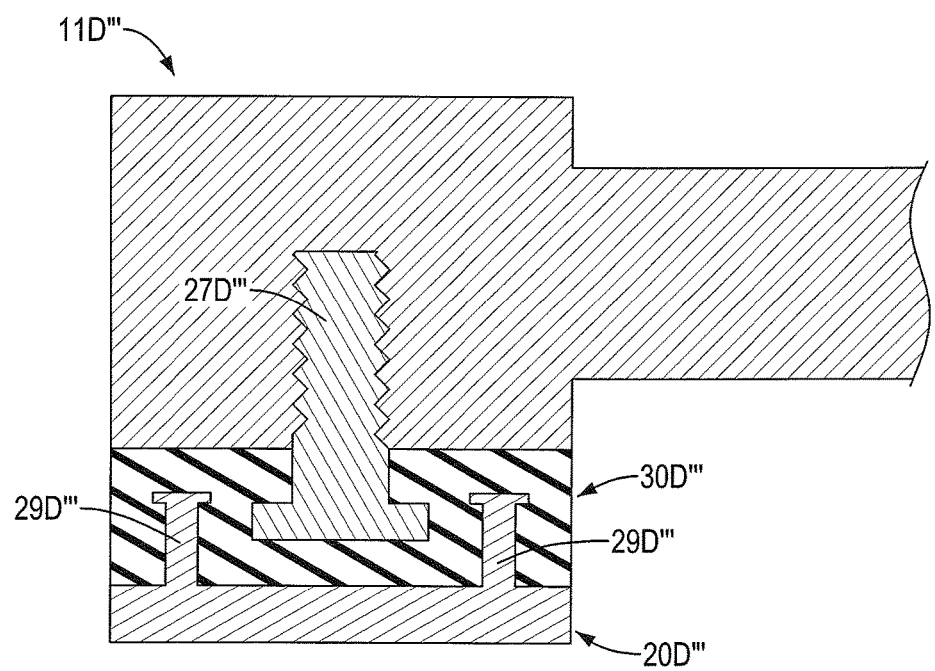
FIG. 23 is an enlarged cross sectional side view of a fourteenth embodiment of a force-limiting and damping device in accordance with the present invention.

With reference to FIG. 23, a fourteenth embodiment of a force-limiting and damping device in accordance with the present invention is substantially the same as the thirteenth embodiment except for the following features. The connecting rod 27D''', the elastic element 30D''', and the tapping element 20D''' are formed with each other as a single piece by injection molding. Then, the connecting rod 27D''' and the tapping element 20D''' are respectively formed on two opposite sides of the elastic element 30D'''. Further, the tapping element 20D''' has multiple reinforcing columns 29D''' formed on and protruding from the tapping element 20D''' and formed in the elastic element 30D''', and this may increase the structural strength between the tapping element 20D''' and the elastic element 30D'''.

Figure 24:
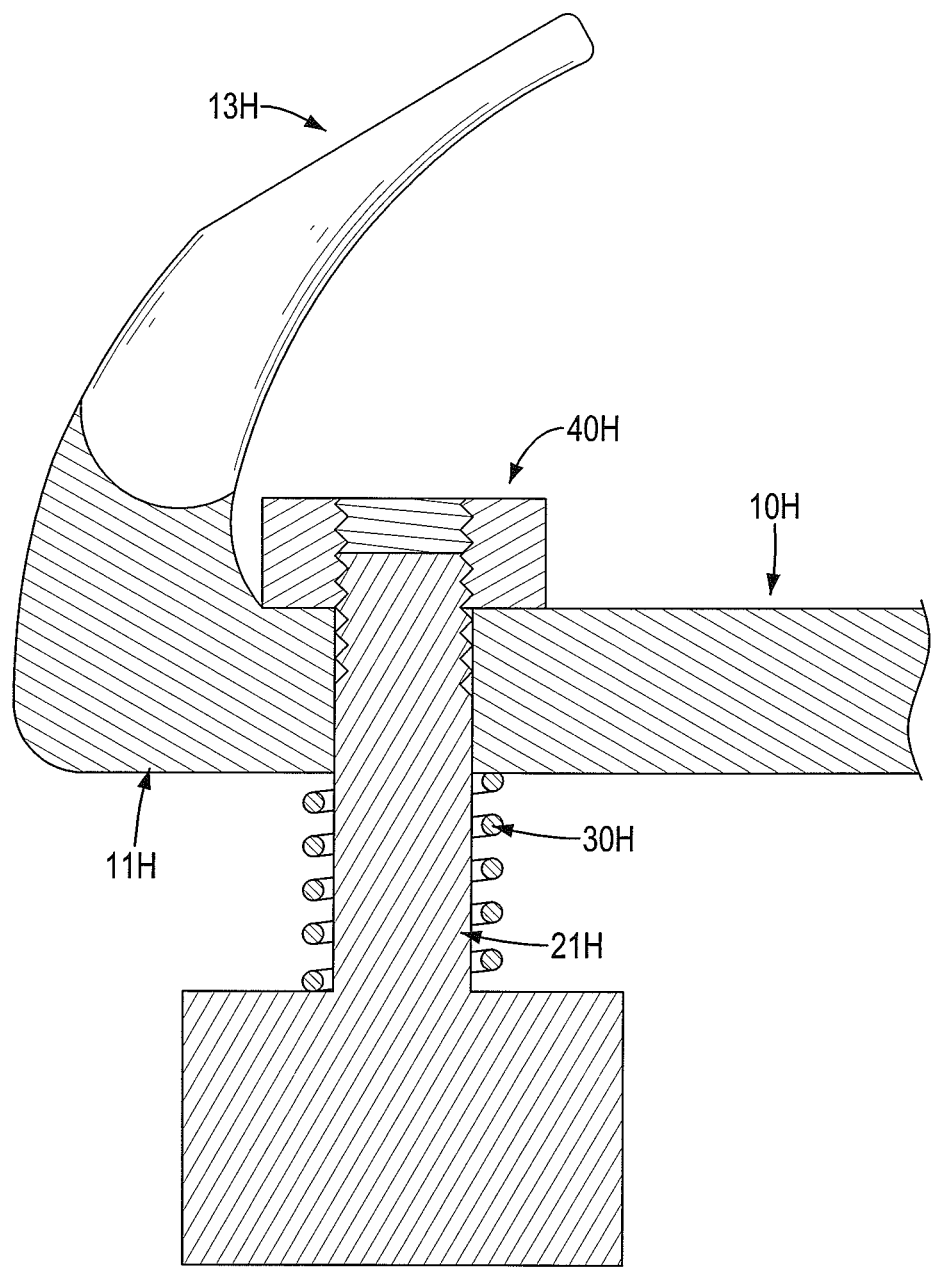
FIG. 24 is an enlarged cross sectional side view of a fifteenth embodiment of a force-limiting and damping device in accordance with the present invention.

With reference to FIG. 24, a fifteenth embodiment of a force-limiting and damping device in accordance with the present invention is substantially the same as the first embodiment except for the following features. The body 10H has a claw 13H formed on and protruding from the top side of the connecting segment 11H and having a gap. Then, the body 10H may pull the nail 60 out of an object by the gap of the claw 13H. The locking element 40H may be a nut in a round shape, square shape or hexagonal shape. When the locking element 40H has a round shape, the user may rotate the locking element 40H by hands to adjust the position of the locking element 40H relative to the mounting segment 21H. When the locking element 40H has a square or hexagonal shape, the user may rotate the locking element 40H by a wrench to adjust the position of the locking element 40H relative to the mounting segment 21H. Additionally, the elastic element 30H may be a spring, a rubber block, a silicone block, a flexible metal block or a flexible block.

Figure 25:
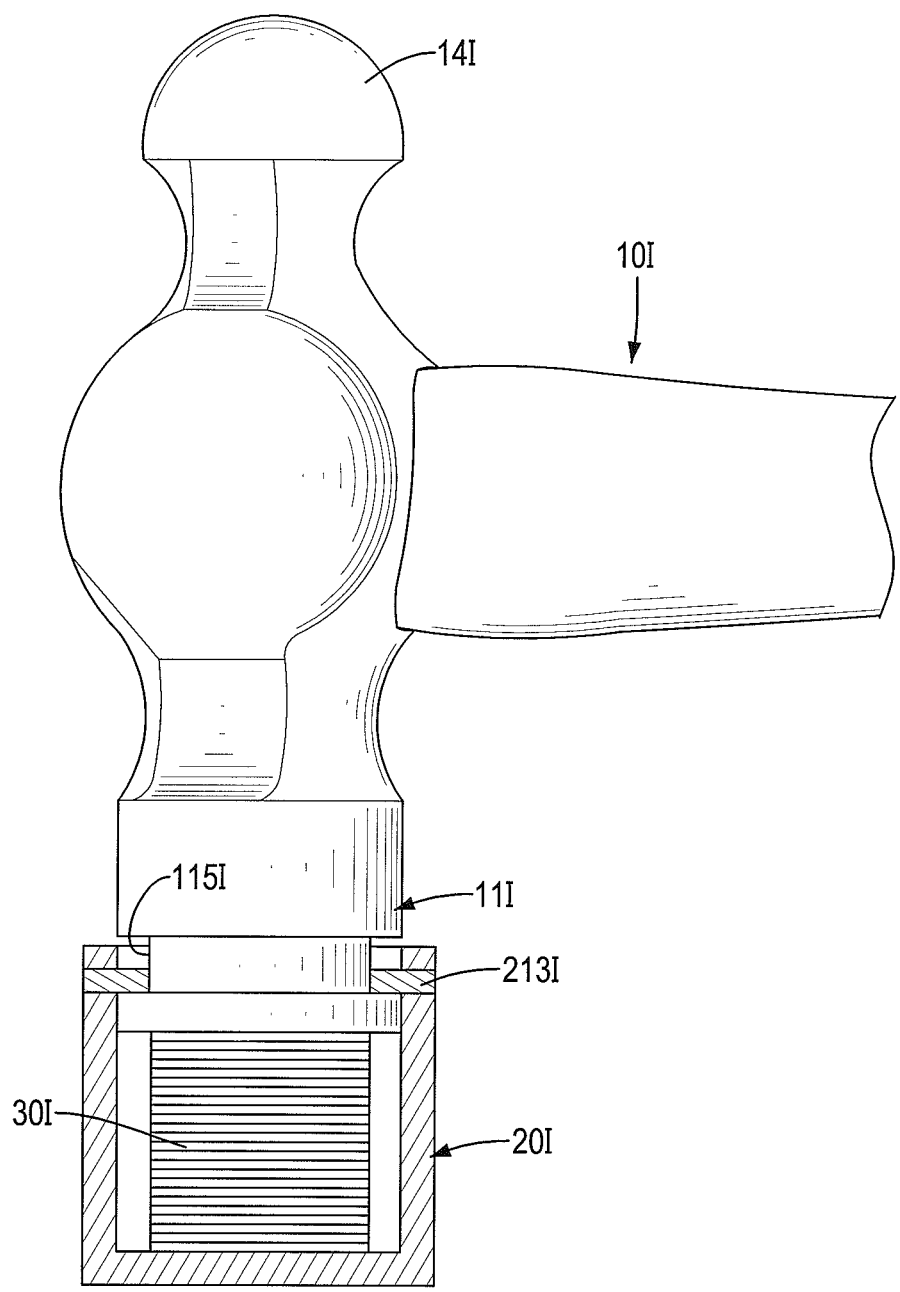
FIG. 25 is an enlarged cross sectional side view of a sixteenth embodiment of a force-limiting and damping device in accordance with the present invention.

With reference to FIG. 25, a sixteenth embodiment of a force-limiting and damping device in accordance with the present invention, the body 10I has a head 14I being round and formed on the top side of the connecting segment 11I, and the tapping element 20I is a cover with an upper opening to movably connect with the connecting segment 11I. The elastic element 30I is mounted between the connecting segment 11I and the tapping element 20I, and may be formed by multiple metal washers stacked with each other or an air cushion that is filled between the connecting segment 11I and the tapping element 20I. Further, the elastic element 30I may be a spring, a rubber block, a silicone block, a flexible metal block or a flexible block. Additionally, the connecting segment 11I has a limiting recess 115I formed annularly in the external surface of the connecting segment 11I, and the tapping element 20I has at least one positioning pin 213I mounted through the tapping element 20I and extending in the limiting recess 115I to hold the tapping element 20I with the connecting segment 11I.

Figure 26:
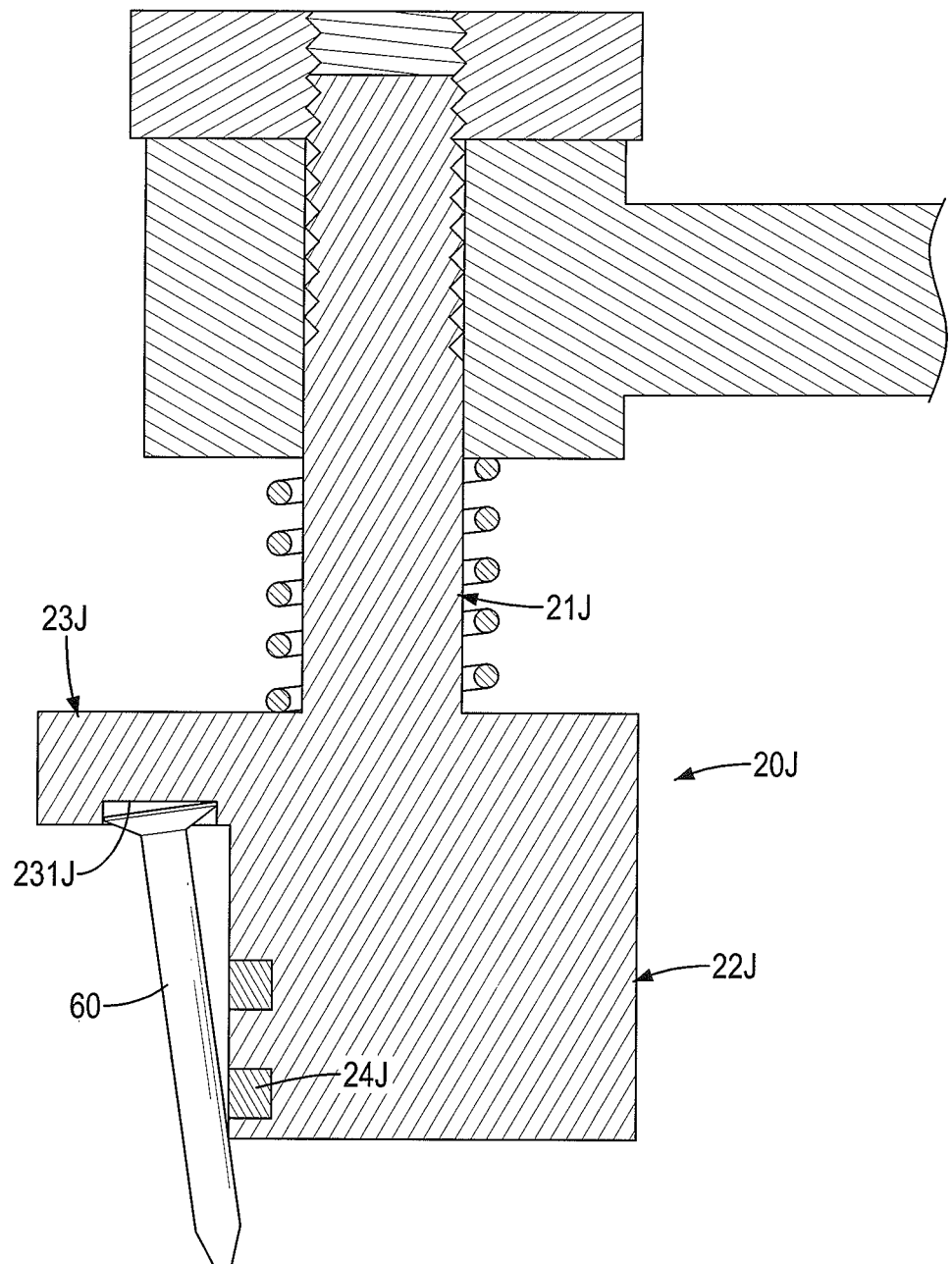
FIG. 26 is an enlarged cross sectional side view of a seventeenth embodiment of a force-limiting and damping device in accordance with the present invention.

With reference to FIG. 26, a seventeenth embodiment of a force-limiting and damping device in accordance with the present invention is substantially the same as the first embodiment except for the following features. The tapping element 20J has a mounting segment 21J, an extending segment 23J and at least one magnetic member 24J. The extending segment 23J is transversally formed on and protrudes from the external surface of the tapping segment 22J and has a bottom and a holding recess 231J formed in the bottom of the extending segment 23J. The at least one magnetic member 24J may be a magnet and is mounted in the tapping segment 22J below the extending segment 23J.

In use, when the nail 60 is connected to the force-limiting and damping device, a head of the nail 60 is positioned in the holding recess 231J of the extending segment 23J and is securely held on the tapping segment 20J by the magnetic attraction of the at least one magnetic member 24J. Then, the user may hold the force-limiting and damping device and the nail 60 by one hand, and this may prevent the user from getting injured when holding the nail 60 by the other hand. In addition, when the user needs to tap the nail 60 at a high position, the user may feel using the force-limiting and damping device by one hand is easy.

Figure 27:
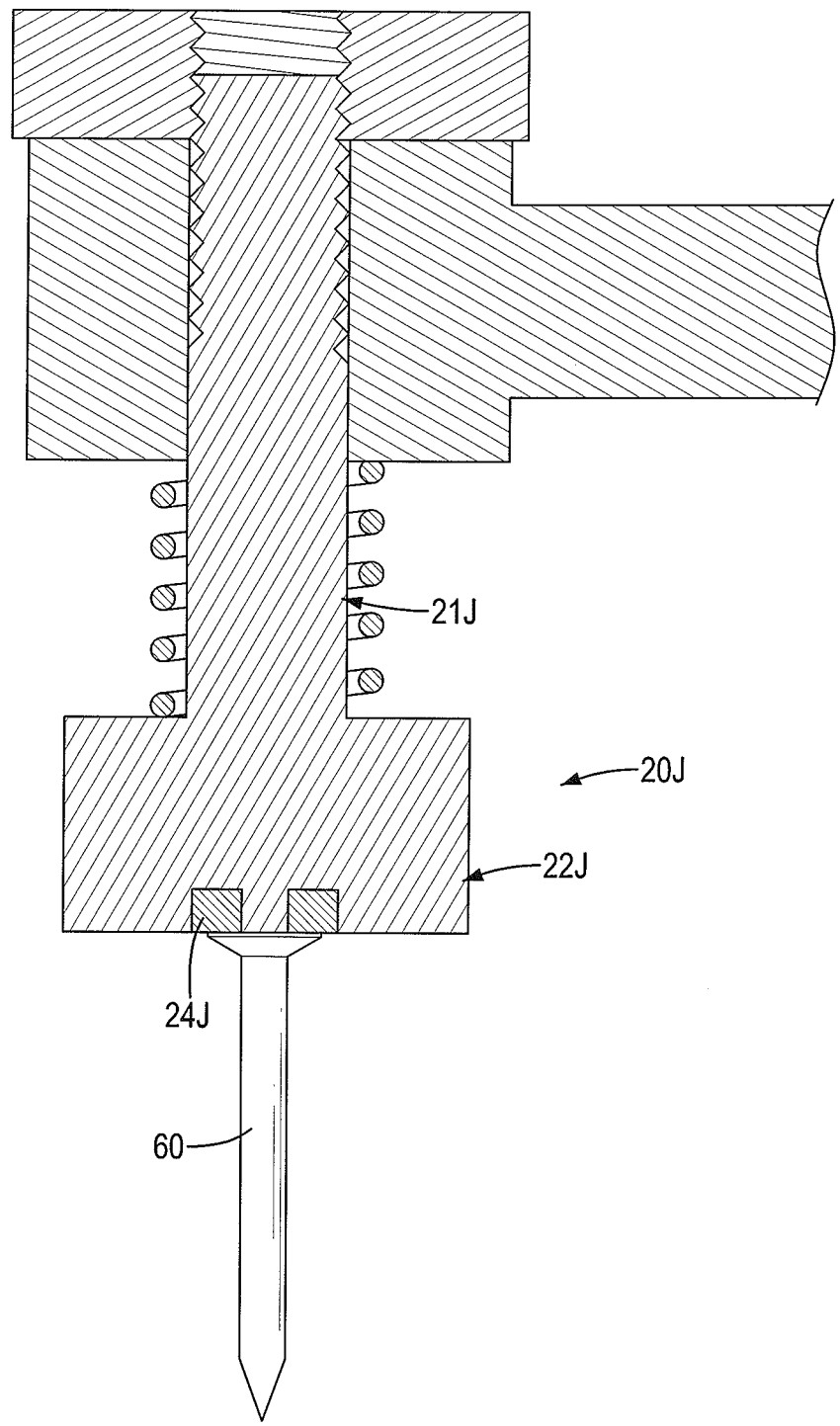
FIG. 27 is an enlarged cross sectional side view of an eighteenth embodiment of a force-limiting and damping device in accordance with the present invention.
Figure 28:
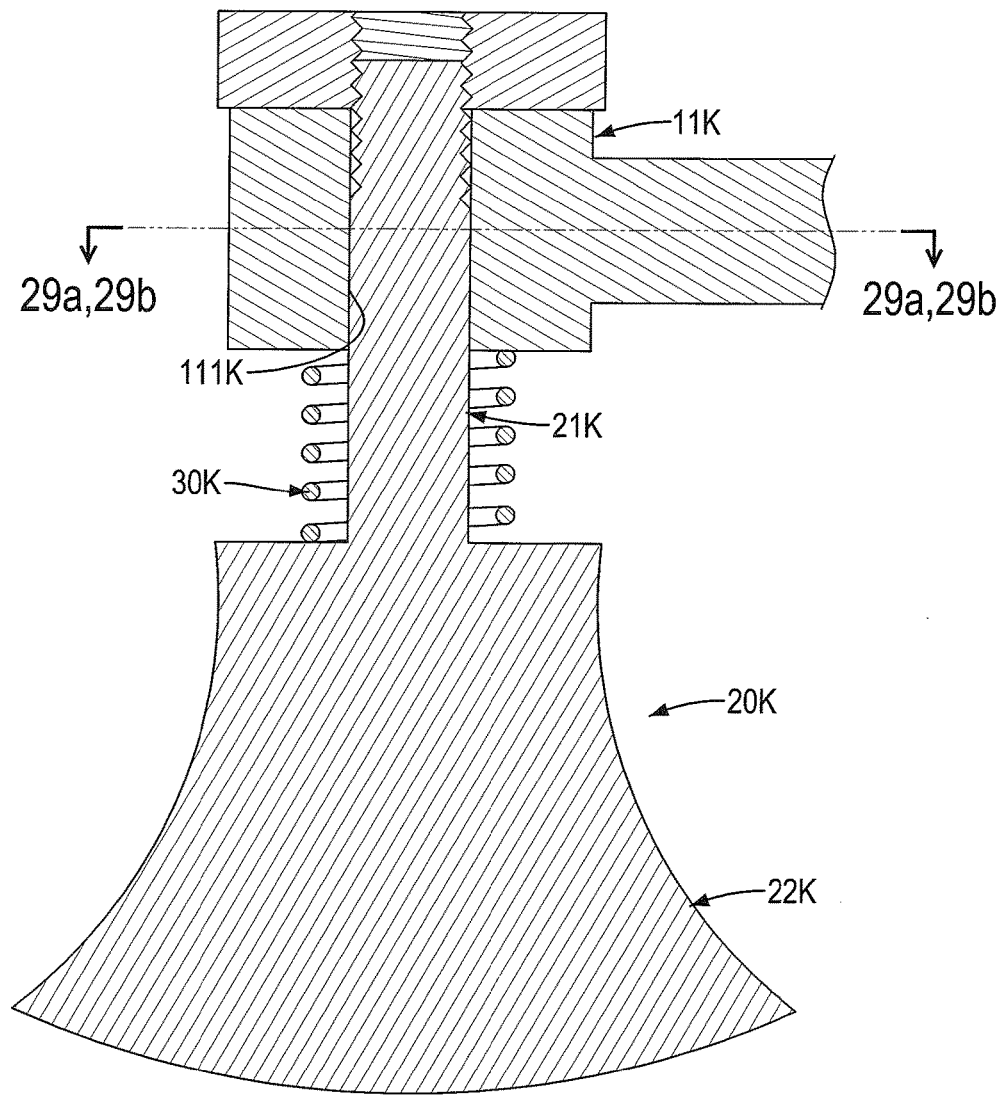
FIG. 28 is an enlarged cross sectional side view of a nineteenth embodiment of a force-limiting and damping device in accordance with the present invention.

With reference to FIG. 27, in an eighteenth embodiment of a force-limiting and damping device in accordance with the present invention, at least one magnetic member 24J is mounted in the bottom of the tapping segment 22J, and the user may tap the nail 60 by one hand.

Figure 29A:
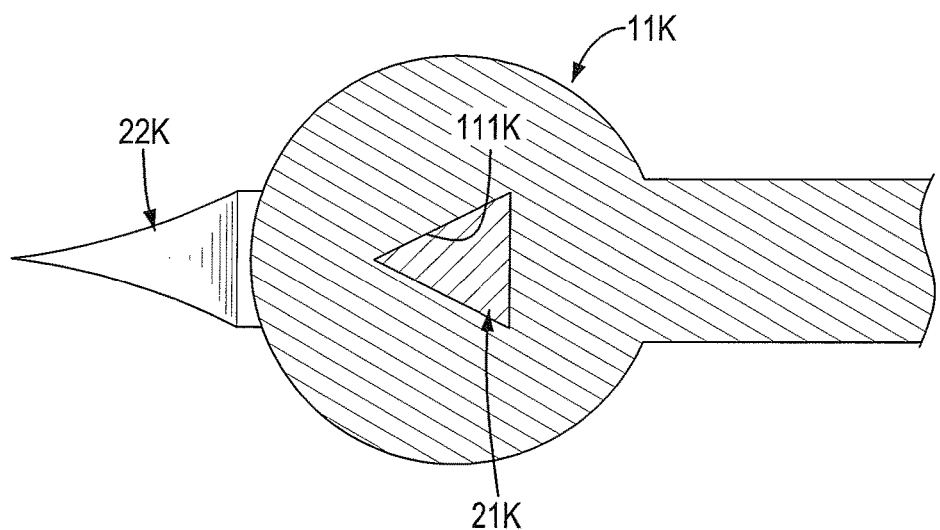
FIGS. 29a and 29b are enlarged and cross sectional top views of the force-limiting and damping device along line 29a-29a and line 29b-29b in FIG. 28.
Figure 29B:
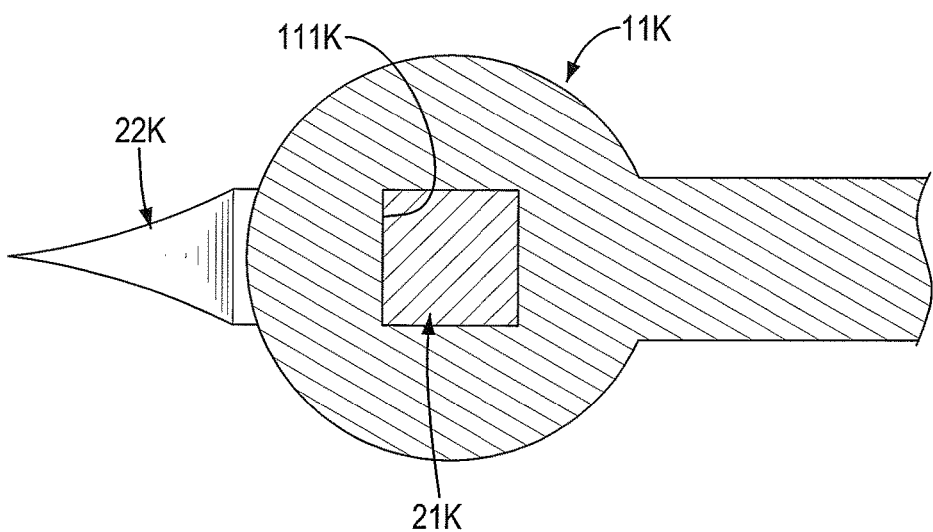
Figure 30:
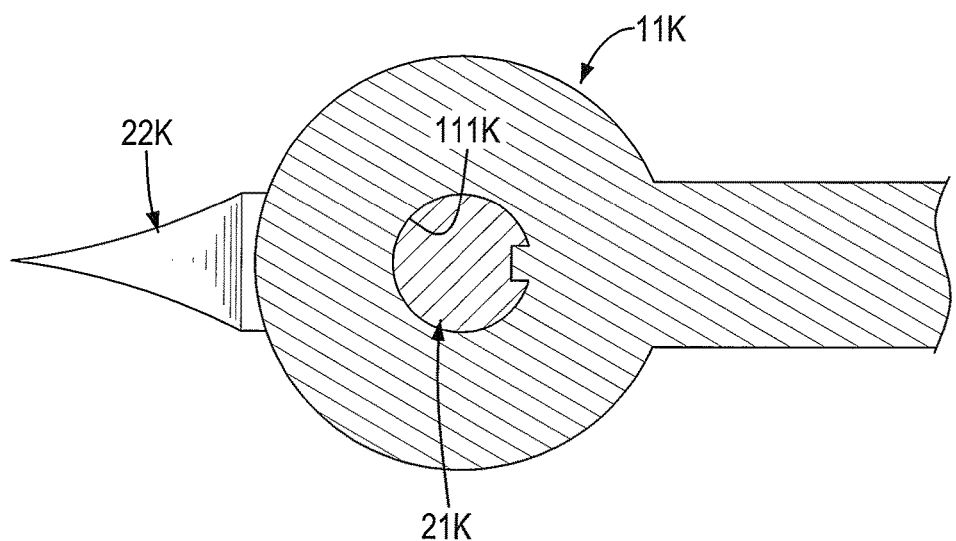
FIG. 30 is another enlarged and cross sectional top view of the force-limiting and damping device in FIG. 28.

With reference to FIGS. 28, 29a, 29b, and 30, a nineteenth embodiment of a force-limiting and damping device in accordance with the present invention is substantially the same as the first embodiment except for the following features. The mounting hole 111K of the connecting segment 11K may be a triangular hole as shown in FIG. 29a, a square hole as shown in FIG. 29b or a circular hole with a protrusion as shown in FIG. 30, and the mounting segment 21K of the tapping element 20K has a cross section corresponding to that of the mounting hole 111K. Then, the tapping element 20K may be moved up or down relative to the connecting segment 11K without rotating relative to the connecting segment 11K. Further, the tapping element 20K is an axe blade, and this enables the force-limiting and damping device to be a hatchet that may provide a force-limiting and damping effect. Additionally, the elastic element 30K may be a spring, a rubber block, a silicone block, a flexible metal block or a flexible block.

Figure 31:
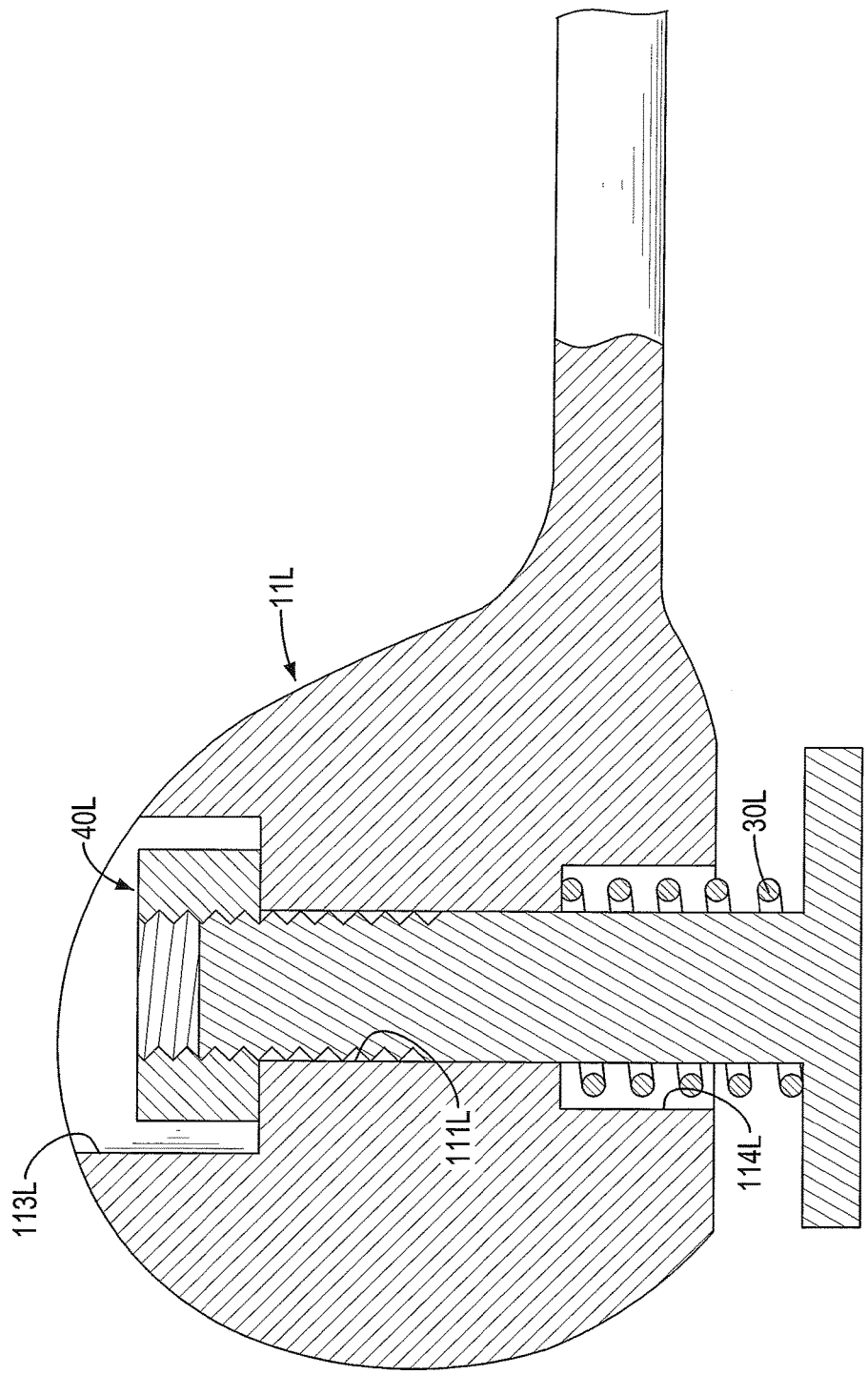
FIG. 31 is an enlarged cross sectional side view of a twentieth embodiment of a force-limiting and damping device in accordance with the present invention.

With reference to FIG. 31, in a twentieth embodiment of a force-limiting and damping device in accordance with the present invention, the connecting segment 11L is a spheroid such as a head of a golf club and has an upper recess 113L and a lower recess 114L. The upper recess 113L is formed in the top side of the connecting segment 11L and communicates with the mounting hole 111L, and the lower recess 114L is formed in the bottom side of the connecting segment 11L and communicates with the mounting hole 111L. Then, the force-limiting and damping device is a golf club that may provide a force-limiting and damping effect.

When the force-limiting and damping device hits a golf ball, the deformation of the golf ball may be reduced by the delayed rebound and damping effect, and this may enable the golf ball to get more energy and may fly farther. Additionally, since the contacting time between the force-limiting and damping device and the golf ball is increased, the user may control the flying direction of the golf ball more accurately to improve the accuracy of the golf ball lie.

Figure 32:
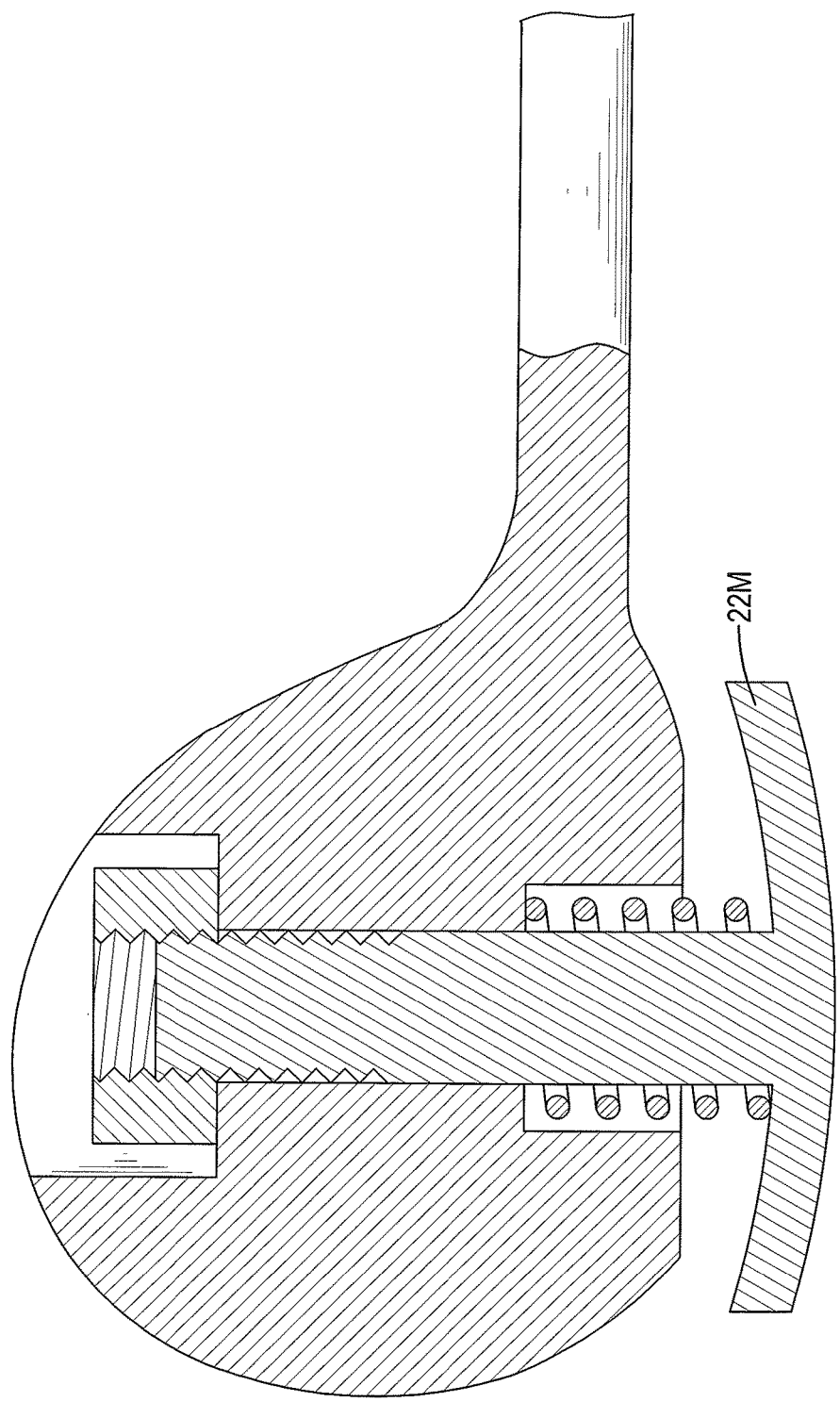
FIG. 32 is an enlarged cross sectional side view of a twenty-first embodiment of a force-limiting and damping device in accordance with the present invention.

With reference to FIG. 32, a twenty-first embodiment of a force-limiting and damping device in accordance with the present invention is substantially the same as the twentieth embodiment except for the following features. The tapping segment 22M is a curved panel that is curved upwardly.

Figure 33:
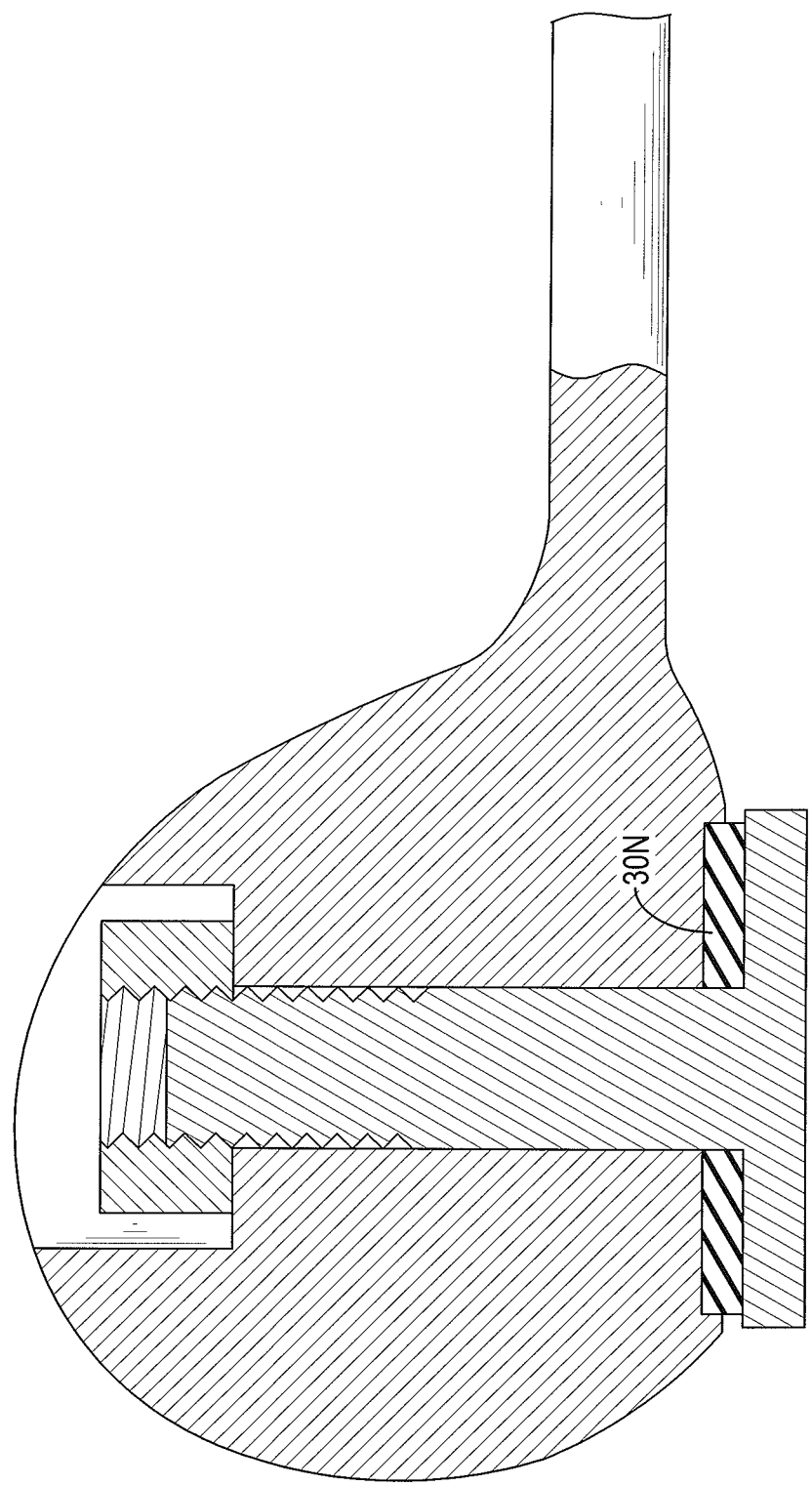
FIG. 33 is an enlarged cross sectional side view of a twenty-second embodiment of a force-limiting and damping device in accordance with the present invention.

With reference to FIG. 33, a twenty-second embodiment of a force-limiting and damping device in accordance with the present invention is substantially the same as the twentieth embodiment except for the following features. The elastic element 30N is an annular rubber block or a flexible block.

Figure 34:
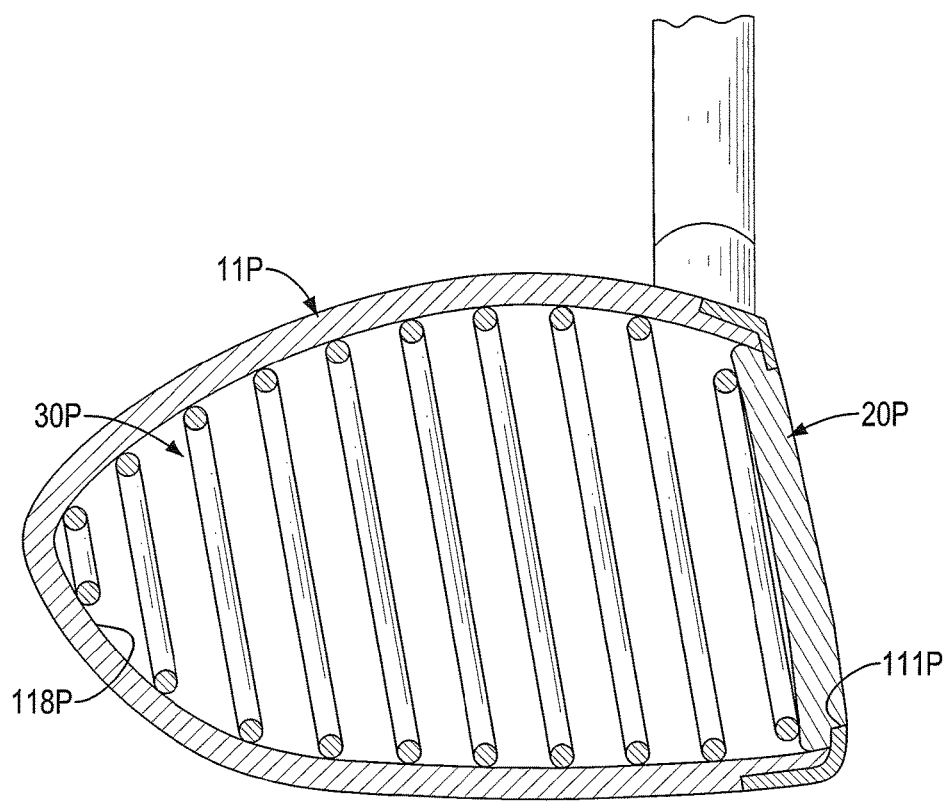
FIG. 34 is an enlarged cross sectional side view of a twenty-third embodiment of a force-limiting and damping device in accordance with the present invention.

With reference to FIG. 34, a twenty-third embodiment of a force-limiting and damping device in accordance with the present invention is substantially the same as the twentieth embodiment except for the following features. The connecting segment 11P has a hollow receiving recess 118P, and the mounting hole 111P is formed at a side of the connecting segment 11P and communicates with the receiving recess 118P. Furthermore, a cover is connected to the side of the connecting segment 11P, and the mounting hole 111P is formed through the cover to communicate with the receiving recess 118P. The tapping element 20P is mounted in the receiving recess 118P and extends out of the connecting segment 11P via the mounting hole 111P. The elastic element 30P is mounted in the receiving recess 118P and abuts the tapping element 20P. Then, the tapping element 20P may be moved relative to the connecting segment 11P by compressing the elastic element 30P.

Figure 35:
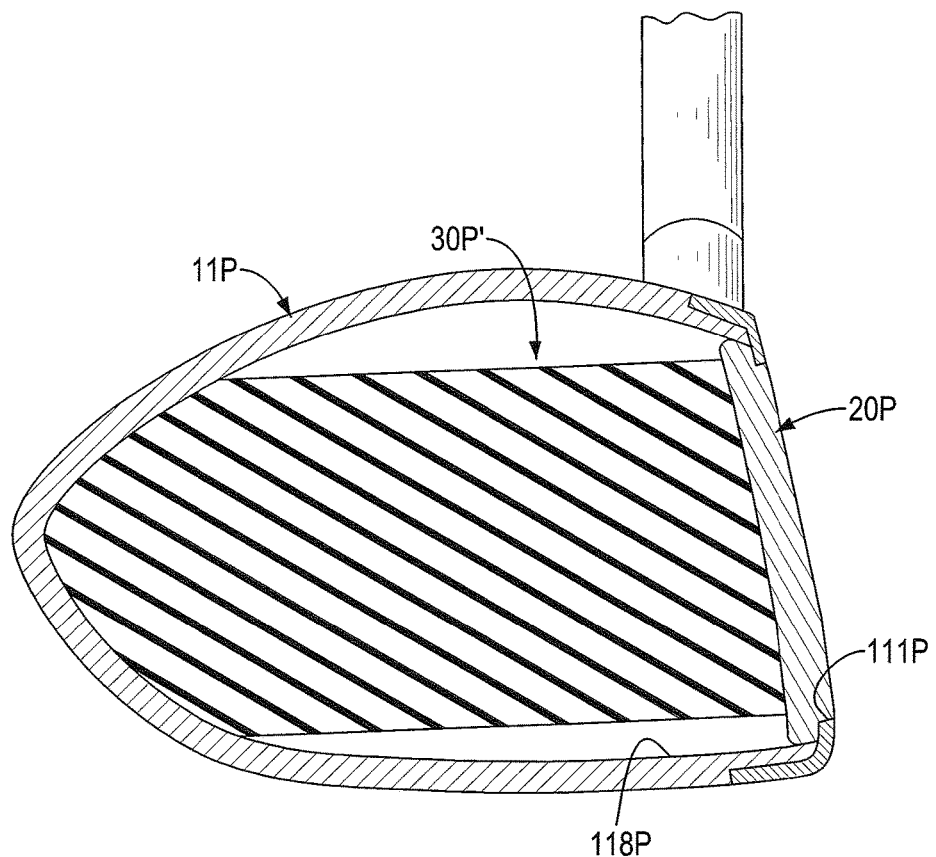
FIG. 35 is an enlarged cross sectional side view of a twenty-fourth embodiment of a force-limiting and damping device in accordance with the present invention.

With reference to FIG. 35, a twenty-fourth embodiment of a force-limiting and damping device in accordance with the present invention is substantially the same as the twenty-third embodiment except for the following features. The elastic element 30P' is a rubber block, a silicone block, a flexible metal block or a flexible block.

Figure 36:
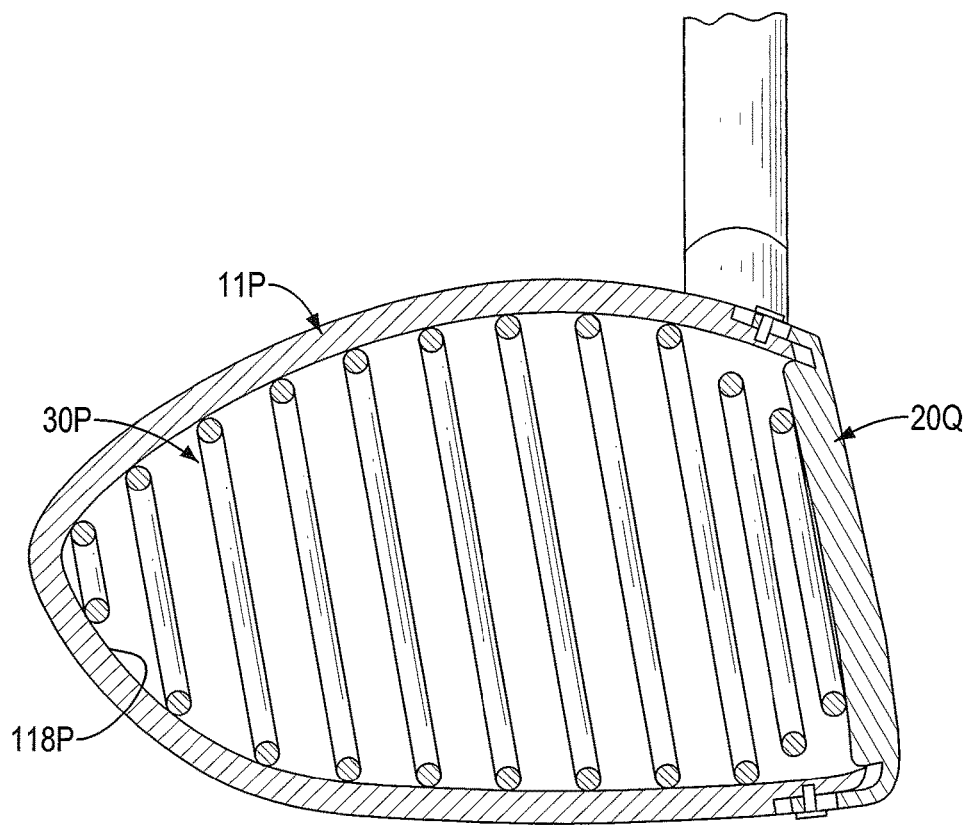
FIG. 36 is an enlarged cross sectional side view of a twenty-fifth embodiment of a force-limiting and damping device in accordance with the present invention.

With reference to FIG. 36, a twenty-fifth embodiment of a force-limiting and damping device in accordance with the present invention is substantially the same as the twenty-third embodiment except for the following features. The tapping element 20Q is movably connected to the connecting segment 11P and abuts the elastic element 30P by elongated slots and pins between the connecting segment 11P and the tapping element 20Q.

According to the above-mentioned structural relationships and the features, the structure of the force-limiting and damping device is simplified, and this is convenient in manufacture, maintenance and replacement. Furthermore, the elastic element 30, 30C, 30D, 30E, 30F, 30Q 30I, 30K, 30L, 30N, 30P, 30P' is mounted between the connecting segment 11, 11D, 11E, 11F, 11H, 11I, 11K, 11L, 11P of the body 10, 10H and the tapping segment 22, 22B, 22C, 22E, 22F, 22G, 22J, 22K or between the connecting segment 11, 11D, 11E, 11F, 11H, 11I, 11K, 11L, 11P of the body 10, 10H and the locking element 40, 40E, 40G 40H, 40L. Then, the user's may be reminded of the tapping force by observing the compression extent of the elastic element 30, 30C, 30D, 30E, 30F, 30G 30I, 30K, 30L, 30N, 30P, 30P', and this may provide a force-limiting effect to the user.

In addition, the force-limiting and damping device may provide a delayed rebound and damping effect to the reaction force that is generated when the tapping segment 22, 22B, 22C, 22D, 22E, 20E', 22F, 22G, 22J, 22K, 22M is tapped on an object, and this may increase the contacting time between the tapping segment 22, 22B, 22C, 22D, 22E, 20E', 22F, 22G, 22J, 22K, 22M and the nail 60 to prevent the nail 60 from bending or deflecting, and to reduce noise and the loss of energy. Furthermore, the numbers and time of tapping the nails 60 can be reduced relatively. Additionally, the force-limiting and damping device may reduce the uncomfortable feeling of the user and the pain of the patient, and the user may hold the body 10, 10H securely to tap. Further, the force-limiting and damping device is simplified and may provide different elastic tensions of the elastic element 30, 30C, 30D, 30E, 30F, 30G, 30H, 30I, 30K, 30L, 30N, 30P, 30P' by replacing the elastic element 30, 30C, 30D, 30E, 30F, 30G, 30H, 30I, 30K, 30L, 30N, 30P, 30P' with different elastic forces or by rotating the locking element 40, 40E, 40G, 40H, 40L easily. Therefore, the force-limiting and damping device of the present invention may provide a damping effect to a user, may provide a high stability in use and may be easily adjusted.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A force-limiting and damping device comprising:
   a body, being an elongated shaft and having
      a front end;
      a rear end;
      a connecting segment formed on and protruding from the front end of the body and having
         a top side;
         a bottom side;
         an external surface; and
         a mounting hole axially formed through the top side and the bottom side of the connecting segment; and
      a holding segment formed on the rear end of the body and being opposite the connecting segment;
   a tapping element connected to the body to move relative to the connecting segment, and having
      a mounting segment movably connected to the connecting segment of the body, extending through the mounting hole, and having
         an external surface;
         a holding end extending out of the top side of the connecting segment via the mounting hole;
         a forming end extending out of the bottom side of the connecting segment via the mounting hole; and
         a locking structure deposited on the external surface of the mounting segment adjacent to the holding end of the mounting segment; and
      a tapping segment deposited on the forming end of the mounting segment, being opposite the locking structure, mounted below the connecting segment, and having a tapping face deposited on a bottom of the tapping segment;
   an elastic element mounted on the mounting segment of the tapping element, and abutting against the connecting segment of the body and the tapping segment of the tapping element, and having a preset compression force; and
   a locking element connected to the mounting segment of the tapping element, abutting the connecting segment of the body to hold the elastic element between the connecting segment and the tapping segment, and having
      a top side;
      a bottom side;
      a locking hole formed through the bottom side of the locking element without forming through the top side of the locking element, aligning with the mounting hole of the connecting segment, and connected to the locking structure of the mounting segment;
   wherein a position of the locking element relative to the locking structure of the mounting segment is fixed;
   wherein during a tapping process, the tapping element is moved toward the body to push against the elastic element, a user is reminded of a tapping force by identifying a compressed extent of the elastic element to determine the tapping force is larger or smaller than the preset compression force of the elastic element, and the elastic element absorbs a reaction that is generated by the tapping element.

2. The force-limiting and damping device as claimed in claim 1, wherein the elastic element is mounted on the mounting segment between the connecting segment and the tapping segment, and is a spring, a rubber block, a silicone block, metal washers, a flexible metal block or a flexible block.

3. The force-limiting and damping device as claimed in claim 1, wherein the tapping segment is integrally formed with the mounting segment as a single piece.

4. The force-limiting and damping device as claimed in claim 3, wherein the tapping segment has
   an external surface; and a chamfered face annularly formed on the external surface of the tapping segment adjacent to the tapping face of the tapping segment.

5. The force-limiting and damping device as claimed in claim 3, wherein the tapping segment is made of a magnetic metal block to provide an attracting effect for nails.

6. The force-limiting and damping device as claimed in claim 3, wherein the tapping element has
an extending segment transversally formed on and protruding from the external surface of the tapping segment and having a bottom and a holding recess formed in the bottom of the extending segment; and
at least one magnetic member mounted in the tapping segment below the extending segment.

7. The force-limiting and damping device as claimed in claim 3, wherein the tapping element has at least one magnetic member mounted in the bottom of the tapping segment to provide an attracting effect for nails.

8. The force-limiting and damping device as claimed in claim 3, wherein the tapping face of the tapping segment is made of metal, polyethylene, plastic, rubber, silicone, wood or leather, and is planar, spherical or in any other shape.

9. The force-limiting and damping device as claimed in claim 3, wherein the body has a claw formed on and protruding from the top side of the connecting segment.

10. The force-limiting and damping device as claimed in claim 4, wherein the holding segment has an external surface and a skidproof structure deposited on the external surface of the holding segment.

11. The force-limiting and damping device as claimed in claim 1, wherein the connecting segment and the locking element are attracted to each other by a magnetic force.

12. The force-limiting and damping device as claimed in claim 11, wherein the tapping segment has
an external surface; and
a chamfered face annularly formed on the external surface of the tapping segment adjacent to the tapping face of the tapping segment.

13. The force-limiting and damping device as claimed in claim 11, wherein the tapping segment is made of a magnetic metal block to provide an attracting effect for nails.

14. The force-limiting and damping device as claimed in claim 11, wherein the tapping element has
an extending segment transversally formed on and protruding from the external surface of the tapping segment and having a bottom and a holding recess formed in the bottom of the extending segment; and
at least one magnetic member mounted in the tapping segment below the extending segment.

15. The force-limiting and damping device as claimed in claim 11, wherein the tapping element has at least one magnetic member mounted in the bottom of the tapping segment to provide an attracting effect for nails.

16. The force-limiting and damping device as claimed in claim 11, wherein the tapping face of the tapping segment is made of metal, polyethylene, plastic, rubber, silicone, wood or leather, and is planar, spherical or in any other shape.

17. The force-limiting and damping device as claimed in claim 11, wherein the body has a claw formed on and protruding from the top side of the connecting segment.

18. The force-limiting and damping device as claimed in claim 11, wherein the holding segment has an external surface and a skidproof structure deposited on the external surface of the holding segment.

19. The force-limiting and damping device as claimed in claim 1, wherein the mounting segment has a threaded section formed on the external surface of the mounting segment adjacent to the forming end of the mounting segment, and being opposite the locking structure;
the tapping segment has
a fixed ring securely connected to the threaded section of the mounting segment and abutting the elastic element; and
a tapping cap securely mounted around the fixed ring at a bottom portion of the tapping element; and
the tapping face of the tapping segment is formed on a bottom of the tapping cap.

20. The force-limiting and damping device as claimed in claim 19, wherein
the threaded section is axially formed in the forming end of the mounting segment opposite the locking structure;
the fixed ring is connected to the threaded section; and
the tapping cap is an annular ring and is connected to the fixed ring.

21. The force-limiting and damping device as claimed in claim 20, wherein the tapping element has at least one magnetic member mounted in the bottom of the tapping segment to provide an attracting effect for nails.

22. The force-limiting and damping device as claimed in claim 19, wherein the tapping segment has
an external surface; and
a chamfered face annularly formed on the external surface of the tapping segment adjacent to the tapping face of the tapping segment.

23. The force-limiting and damping device as claimed in claim 19, wherein the tapping segment is made of a magnetic metal block to provide an attracting effect for nails.

24. The force-limiting and damping device as claimed in claim 19, wherein the tapping element has
an extending segment transversally formed on and protruding from the external surface of the tapping segment and having a bottom and a holding recess formed in the bottom of the extending segment; and
at least one magnetic member mounted in the tapping segment below the extending segment.

25. The force-limiting and damping device as claimed in claim 19, wherein the tapping element has at least one magnetic member mounted in the bottom of the tapping segment to provide an attracting effect for nails.

26. The force-limiting and damping device as claimed in claim 19, wherein the tapping face of the tapping segment is made of metal, polyethylene, plastic, rubber, silicone, wood or leather, and is planar, spherical or in any other shape.

27. The force-limiting and damping device as claimed in claim 19, wherein the body has a claw formed on and protruding from the top side of the connecting segment.

28. The force-limiting and damping device as claimed in claim 19, wherein the holding segment has an external surface and a skidproof structure deposited on the external surface of the holding segment.

29. The force-limiting and damping device as claimed in claim 1, wherein the locking element has an adjusting ring rotatably mounted on the mounting segment between the elastic element and the tapping segment to hold the elastic element between the connecting segment and the adjusting ring.

30. The force-limiting and damping device as claimed in claim 29, wherein the tapping element has at least one magnetic member mounted in the bottom of the tapping segment to provide an attracting effect for nails.

31. The force-limiting and damping device as claimed in claim 1, wherein the locking element has an adjusting ring rotatably mounted on a bottom portion of the connecting segment between the elastic element and the connecting segment to hold the elastic element between the adjusting ring and the tapping segment.

32. The force-limiting and damping device as claimed in claim 31, wherein the tapping element has at least one magnetic member mounted in the bottom of the tapping segment to provide an attracting effect for nails.

33. The force-limiting and damping device as claimed in claim 1, wherein
the mounting hole is formed through the top side and the bottom side of the connecting segment and has two inner diameters, one of the inner diameters of the mounting hole formed at the top side of the connecting segment and being wider than the other inner diameter that is formed at the bottom side of the connecting segment;
the connecting segment has a chamber formed in the connecting segment and communicating with the mounting hole;
the mounting segment of the tapping element is mounted in the chamber of the connecting segment via the mounting hole at the top side of the connecting segment, and extends out of the bottom side of the connecting segment via the mounting hole at the bottom side of the connecting segment;
the tapping segment is integrally formed with the mounting segment as a single piece and extends out of the bottom side of the connecting segment via the mounting hole;
the locking element is rotatably connected to the connecting segment of the body, abuts the elastic element to hold the elastic element between the mounting segment and the locking element, and extending into the chamber of the connecting segment; and
the elastic element is mounted in the chamber of the connecting segment, and abuts the mounting segment and the locking element.

34. The force-limiting and damping device as claimed in claim 33, wherein the tapping segment is connected to the mounting segment by screwing without forming as a single piece.

35. The force-limiting and damping device as claimed in claim 34, wherein the elastic element is mounted between the connecting segment and the tapping element by multiple springs, rubber blocks, silicone blocks, metal washers, flexible metal blocks or flexible blocks stacked with each other.

36. The force-limiting and damping device as claimed in claim 34, wherein the tapping element has
an extending segment transversally formed on and protruding from the external surface of the tapping segment and having a bottom and a holding recess formed in the bottom of the extending segment; and
at least one magnetic member mounted in the tapping segment below the extending segment.

37. The force-limiting and damping device as claimed in claim 33, wherein the elastic element is mounted between the connecting segment and the tapping element by multiple springs, rubber blocks, silicone blocks, metal washers, flexible metal blocks or flexible blocks stacked with each other.

38. The force-limiting and damping device as claimed in claim 33, wherein the tapping segment is made of a magnetic metal block to provide an attracting effect for nails.

39. The force-limiting and damping device as claimed in claim 33, wherein the tapping element has
an extending segment transversally formed on and protruding from the external surface of the tapping segment and having a bottom and a holding recess formed in the bottom of the extending segment; and
at least one magnetic member mounted in the tapping segment below the extending segment.

40. The force-limiting and damping device as claimed in claim 33, wherein the tapping element has at least one magnetic member mounted in the bottom of the tapping segment to provide an attracting effect for nails.

41. The force-limiting and damping device as claimed in claim 33, wherein the tapping face of the tapping segment is made of metal, polyethylene, plastic, rubber, silicone, wood or leather, and is planar, spherical or in any other shape.

42. The force-limiting and damping device as claimed in claim 33, wherein the body has a claw formed on and protruding from the top side of the connecting segment.

43. The force-limiting and damping device as claimed in claim 33, wherein the holding segment has an external surface and a skidproof structure deposited on the external surface of the holding segment.

44. The force-limiting and damping device as claimed in claim 1, wherein
the connecting segment has
a chamber formed in the connecting segment and communicating with the mounting hole; and
an outer thread formed on the external surface of the connecting segment adjacent to the bottom side of the connecting segment;
the mounting segment of the tapping element has a limiting cover connected to the outer thread of the connecting segment to enable the tapping segment to extend out of the bottom side of the connecting segment via the limiting cover;
the locking element is rotatably connected to the connecting segment of the body, abuts the elastic element to hold the elastic element between the mounting segment and the locking element, and extends into the chamber of the connecting segment; and
the elastic element is mounted in the chamber of the connecting segment and abuts the mounting segment and the locking element.

45. The force-limiting and damping device as claimed in claim 44, wherein the elastic element is mounted between the connecting segment and the tapping element by multiple springs, rubber blocks, silicone blocks, metal washers, flexible metal blocks or flexible blocks stacked with each other.

46. The force-limiting and damping device as claimed in claim 44, wherein the tapping segment is made of a magnetic metal block to provide an attracting effect for nails.

47. The force-limiting and damping device as claimed in claim 44, wherein the tapping element has
an extending segment transversally formed on and protruding from the external surface of the tapping segment and having a bottom and a holding recess formed in the bottom of the extending segment; and
at least one magnetic member mounted in the tapping segment below the extending segment.

48. The force-limiting and damping device as claimed in claim 44, wherein the tapping element has at least one magnetic member mounted in the bottom of the tapping segment to provide an attracting effect for nails.

49. The force-limiting and damping device as claimed in claim 44, wherein the tapping face of the tapping segment is made of metal, polyethylene, plastic, rubber, silicone, wood or leather, and is planar, spherical or in any other shape.

50. The force-limiting and damping device as claimed in claim 44, wherein the body has a claw formed on and protruding from the top side of the connecting segment.

51. The force-limiting and damping device as claimed in claim 44, wherein the holding segment has an external surface and a skidproof structure deposited on the external surface of the holding segment.

52. The force-limiting and damping device as claimed in claim 1, wherein
the elastic element has
a sensor abutting the elastic element; and
a display securely mounted on the top side of the connecting segment and electrically connected to the sensor;
when the elastic element is compressed by the tapping element, the sensor detects the tapping force of the tapping element via the compression force of the elastic element, and the detected tapping force of the tapping element is shown on the display.

53. The force-limiting and damping device as claimed in claim 52, wherein the body has a claw formed on and protruding from the top side of the connecting segment.

54. The force-limiting and damping device as claimed in claim 1, wherein the tapping segment has
an external surface; and
a chamfered face annularly formed on the external surface of the tapping segment adjacent to the tapping face of the tapping segment.

55. The force-limiting and damping device as claimed in claim 1, wherein the tapping segment is made of a magnetic metal block to provide an attracting effect for nails.

56. The force-limiting and damping device as claimed in claim 1, wherein the tapping element has
an extending segment transversally formed on and protruding from the external surface of the tapping segment and having a bottom and a holding recess formed in the bottom of the extending segment; and
at least one magnetic member mounted in the tapping segment below the extending segment.

57. The force-limiting and damping device as claimed in claim 1, wherein the tapping element has at least one magnetic member mounted in the bottom of the tapping segment to provide an attracting effect for nails.

58. The force-limiting and damping device as claimed in claim 1, wherein the tapping face of the tapping segment is made of metal, polyethylene, plastic, rubber, silicone, wood or leather, and is planar, spherical or in any other shape.

59. The force-limiting and damping device as claimed in claim 1, wherein the body has a claw formed on and protruding from the top side of the connecting segment.

60. The force-limiting and damping device as claimed in claim 1, wherein
the mounting hole is a circular hole; and
the mounting segment of the tapping element has a cross section corresponding to the mounting hole to enable the tapping element to move up or down and to rotate relative to the connecting segment.

61. The force-limiting and damping device as claimed in claim 1, wherein
the mounting hole is a polygonal hole; and
the mounting segment of the tapping element has a cross section corresponding to the mounting hole to enable the tapping element to move up or down relative to the connecting segment without rotating.

62. The force-limiting and damping device as claimed in claim 1, wherein the holding segment has an external surface and a skidproof structure deposited on the external surface of the holding segment.

* * * * *